(12) United States Patent
Snedeker et al.

(10) Patent No.: US 12,318,083 B2
(45) Date of Patent: Jun. 3, 2025

(54) SINGLE STRAND SELF-LOCKING SUSPENSION DEVICE FOR MEDICAL USE

(71) Applicant: ZURIMED TECHNOLOGIES AG, Zürich (CH)

(72) Inventors: Jess Snedeker, Zürich (CH); Elias Bachmann, Meilen (CH); Xiang Li, Zumikon (CH)

(73) Assignee: ZURIMED TECHNOLOGIES AG, Zürich (CH)

( * ) Notice: Subject to any disclaimer, the term of this patent is extended or adjusted under 35 U.S.C. 154(b) by 834 days.

(21) Appl. No.: 17/055,582

(22) PCT Filed: May 12, 2019

(86) PCT No.: PCT/EP2019/062116
§ 371 (c)(1),
(2) Date: Nov. 15, 2020

(87) PCT Pub. No.: WO2019/219548
PCT Pub. Date: Nov. 21, 2019

(65) Prior Publication Data
US 2021/0369260 A1 Dec. 2, 2021

(30) Foreign Application Priority Data
May 16, 2018 (EP) .................................... 18172759

(51) Int. Cl.
*A61B 17/04* (2006.01)
*A61B 90/00* (2016.01)
*A61F 2/08* (2006.01)

(52) U.S. Cl.
CPC .......... *A61B 17/0401* (2013.01); *A61B 90/03* (2016.02); *A61B 90/06* (2016.02);
(Continued)

(58) Field of Classification Search
CPC .... A61B 2017/0409; A61B 2017/0404; A61B 2017/0406; A61B 2017/0459;
(Continued)

(56) References Cited

U.S. PATENT DOCUMENTS 6,344,042 B1  2/2002 Curtis et al.
2013/0245686 A1  9/2013 Fallin et al.
(Continued)

FOREIGN PATENT DOCUMENTS

CN  104337590  2/2015
FR  2815843  5/2002

*Primary Examiner* — Majid Jamialahmadi
(74) *Attorney, Agent, or Firm* — JMB Davis Ben-David

(57) ABSTRACT

An implantable suspension device (1) for fixing an elongated flexible implant (G) or tissue (B) in a desired position, comprising a suspension plate (100) and a single suture element (200) engaging with the suspension plate (100) such that the suture element (200) forms an adjustable suspension loop (300) for connecting said implant (G) or tissue (B) to the suspension plate (100), wherein the single suture element (200) comprises a free first end section (201) and a second end section (202), and wherein the single suture element (200) comprises a stopper (20) arranged on the second end section (202), and wherein the suture element (200) forms a locking loop (40) for pressing the first end section (201) against the suspension plate (100) and thereby locking the first end section (201) of the suture element (200) with respect to the suspension plate (100).

15 Claims, 24 Drawing Sheets

Figure 1:
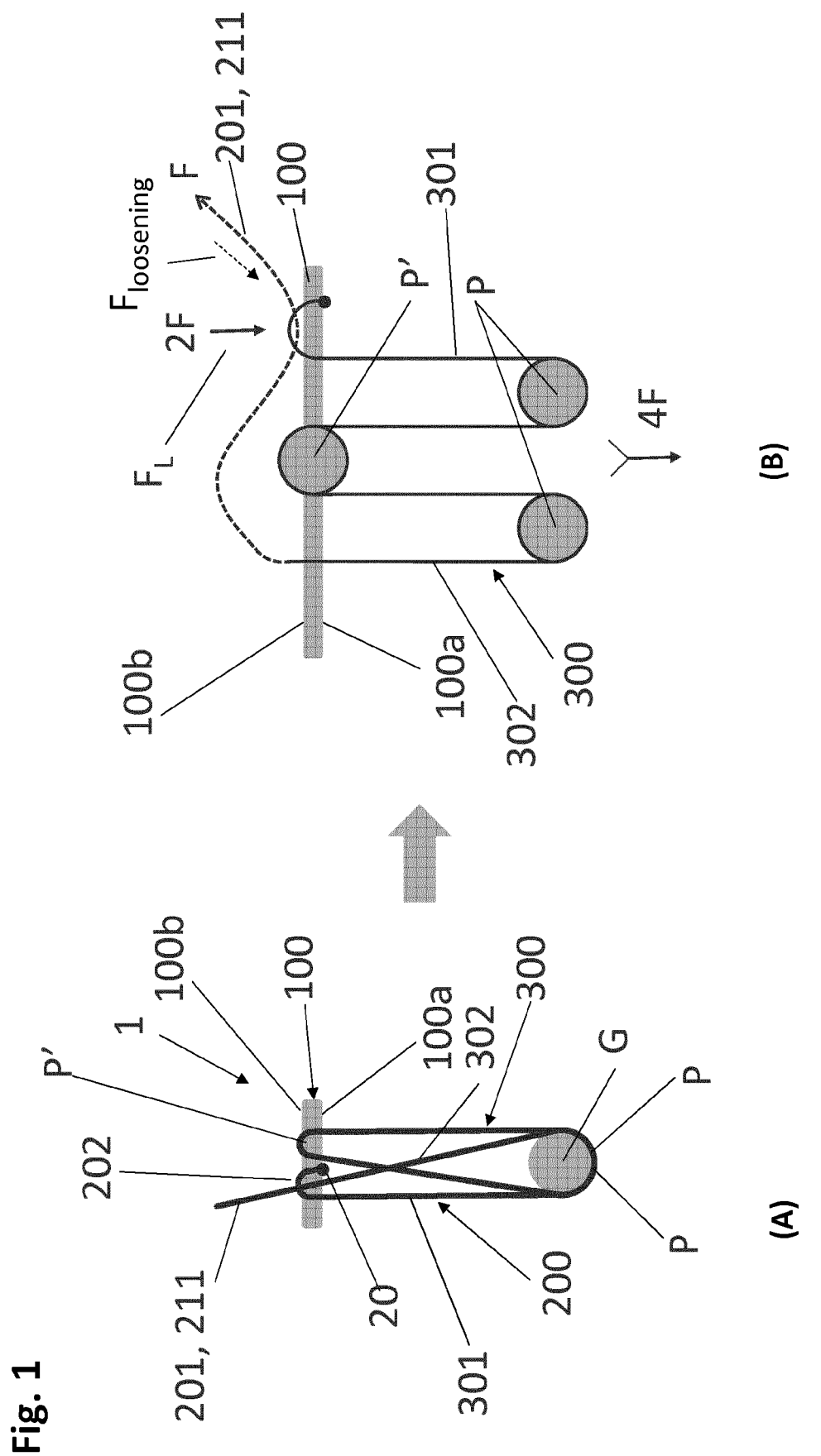

(52) U.S. Cl.
CPC ..... *A61F 2/0811* (2013.01); *A61B 2017/0404* (2013.01); *A61B 2017/0409* (2013.01); *A61B 2017/0459* (2013.01); *A61B 2017/0496* (2013.01); *A61B 2090/034* (2016.02); *A61B 2090/061* (2016.02); *A61B 2090/064* (2016.02); *A61F 2002/0852* (2013.01); *A61F 2002/0882* (2013.01)

(58) Field of Classification Search
CPC .... A61B 2017/0496; A61B 2017/0417; A61B 17/683; A61F 2/0811; A61F 2002/0852
See application file for complete search history.

(56) References Cited

U.S. PATENT DOCUMENTS

| | | | |
|---|---|---|---|
| 2015/0039026 A1* | 2/2015 | Pasquali | A61B 17/06166 606/228 |
| 2015/0112385 A1 | 4/2015 | Perriello et al. | |
| 2016/0151060 A1 | 6/2016 | Albertorio et al. | |
| 2017/0231752 A1 | 8/2017 | Rodriguez et al. | |
| 2018/0221013 A1* | 8/2018 | Marks | A61B 17/0482 |

* cited by examiner

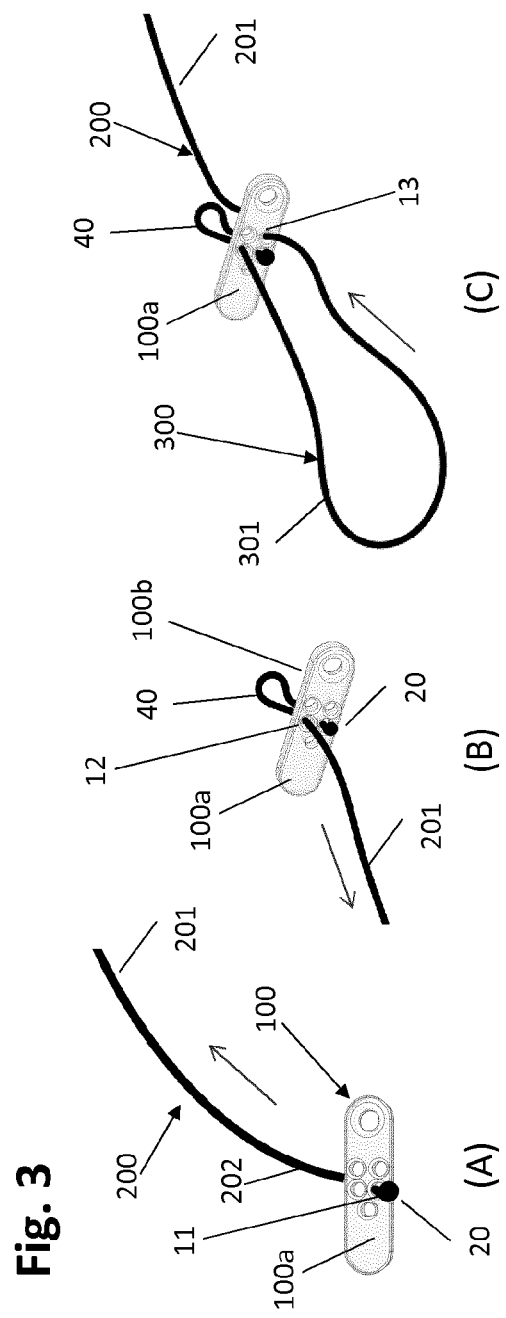

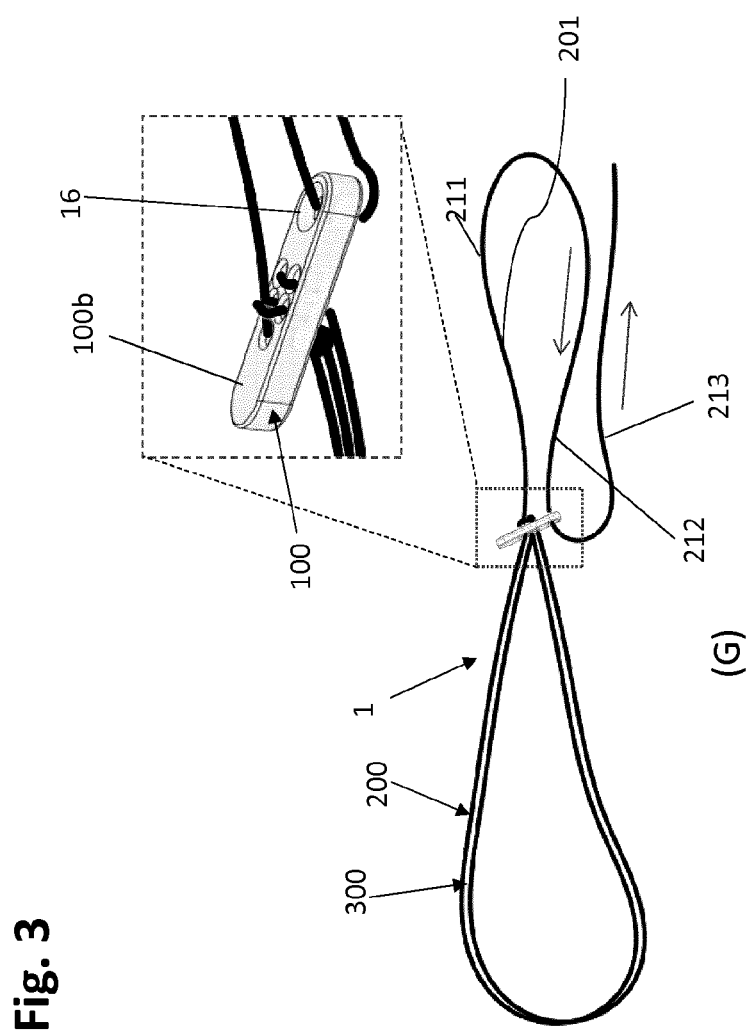

SINGLE STRAND SELF-LOCKING SUSPENSION DEVICE FOR MEDICAL USE

CROSS-REFERENCE TO RELATED APPLICATIONS

This is the U.S. National Stage of International Patent Application No. PCT/EP2019/062116 filed on May 12, 2019, which in turn claims the benefit of European Patent Application No. 18172759.5 filed on May 16, 2018.

The invention relates to an implantable suspension device, particularly for the reconstruction of the anterior cruciate ligament (ACL).

Due to its anatomical location, the ACL is subjected to potentially extreme forces during sports and other physical activities. Rupture of the ACL has been counted as the most frequent and severe of ligament injuries.

For ACL reconstruction suspension devices also denoted as cortical fixation devices (CFD) are often used. Such devices often comprise a plate, also known as button, that helps to secure the tendon or ligament graft to its desired position when performing the anterior cruciate ligament (ACL) reconstruction. Such devices may also be used in conjunction with other ligament or tendon grafts or other flexible (e.g. elongated) members.

In ACL reconstruction, fixation of the graft (e.g. hamstring graft or patellar bone-tendon-bone graft (BTB)) onto the cortex of the femur at the proximal end of the femoral tunnel is a crucial part of a successful procedure.

Here, titanium (or steel)-made plates hold a continuous suspension loop formed by sutures usually made out of polyester, polyethylene or similar material. This loop is the attachment site of the (e.g. hamstring, BTB, or synthetic) graft. Once the graft is attached, the plate or button can be pulled through the tibial or femoral tunnel by temporarily attached sutures until it reaches the cortex of the femur. By either pulling back on the graft or using a second suture to flip the button, the button is pulled flush against the cortex of the femoral bone. The graft can be seen as being suspended from the cortex of the femur.

Variations between devices are present in the state of the art and particularly relate to the way the suspension loop is locked and the length of the suspension loop is adjusted. Particularly, according US2010268273A1 the device comprises two interconnected adjustable eyesplices. Furthermore, EP2777612A1 uses a self-locking knot to secure the suspension loop. Further, the device according to WO2012154922A2 comprises a suture having a first end received within the suture through an open second end of the suture to form a loop having only one free end, wherein the length of the suture between a fixation member and a tissue graft can be adjusted by pulling the free end of the suture.

Based on the above, the problem underlying the present invention is to provide an improved implantable suspension device that allows a fast adjustment and safe securing of a suture element.

This problem is solved by a suspension device having the features of claim 1. Preferred embodiments of this aspect of the present invention are stated in the corresponding sub claims and are described below.

Further aspects of the present invention relate to a method for building a suspension device according to the present invention, a suspension plate, a tool, and a method for forming a stopper on an end section of a suture element.

According to claim 1, an implantable suspension device is disclosed, particularly for use in an anterior cruciate ligament (ACL) reconstruction, which device is configured for fixing an elongated flexible implant (e.g. a ligament or tendon graft) or tissue (such as bone tissue) in a desired position, wherein the suspension device comprises a suspension plate and a single (particularly elongated and flexible) suture element engaging with the suspension plate such that the suture element forms an adjustable suspension loop for connecting said implant or tissue to the suspension plate, wherein the single suture element comprises a free first end section and a second end section, and wherein the single suture element comprises a stopper arranged on the second end section, and wherein the suture element forms a locking loop for pressing the first end section against the suspension plate and thereby locking the first end section of the suture element with respect to the suspension plate.

Thus, advantageously, the suspension device particularly comprises merely one (i.e. exactly one) suture element.

Particularly, the suspension device can be used to fix soft tissue to bone. Further, particularly, the suspension plate is formed out of a biocompatible material, particularly a biocompatible metal, such as titanium or a titanium alloy or stainless steel. Furthermore, the suture element is formed out of one of the following materials: polyethylene, polyester, polypropylene, and other similar biocompatible suture materials.

Further, the suture element can comprise a plurality of fibres connected to one another to form the suture element. However, the suture element can also be formed by a single filament. Particularly, the suture element is pliable.

The suspension device according to the present invention can be used for many indications of fixing or suspending soft tissue to bone, of fixing bone to bone.

Particularly, the suspension device according to the present invention can be used for an anterior cruciate ligament (ACL) reconstruction. Particularly, in case of ACL reconstruction, the front side of the suspension plate is configured to butt against the tibia or femur of the patient, wherein particularly the suspension loop extends through a bore hole drilled into the tibia or femur.

According to an embodiment of the suspension device, the suspension loop is configured to be shortened by pulling on a first pulling section formed by a portion of the first end section of the suture element protruding out the locking loop.

Further, according an embodiment of the suspension device, a load on the suspension loop and/or a length of the suspension loop is proportionally related to a pulling force on the first pulling section/a displacement of the first pulling section. Particularly, this means that the displacement of the pulling strand is proportional to the shortening length of suspension loop, and particularly that the force applied on the graft by the suspension loop is proportional to the pulling force on the first pulling section.

Thus, the load on the suspension loop and the length of the suspension loop can be controlled reliably.

Further, according to an embodiment of the implantable suspension device, a loosening force on the first pulling section is reduced by the suspension loop comprising at least two deflection points movable with respect to the suspension plate (e.g. when the suspension loop is shortened) and at least one deflection point fixed with respect to the suspension plate. Thus—in combination with the locking loop—a self-locking function is achieved, i.e. the suspension loop is a self-locking suspension loop.

In other words, according to an embodiment of the suspension device, the suspension loop comprises at least two deflection points movable with respect to the suspension plate and at least one deflection point fixed to the suspension plate. Thus, particularly, the suspension loop forms a tackle.

In the context of the present invention, a deflection point is a point where the direction of the suture element changes its orientation (sign) so that the suture element is deflected at this point of the suture element. Particularly, the movable deflection points are located at the implant/tissue around which the suspension loop is laid, wherein the fixed deflection point is located at the suspension plate, where the suture element is also deflected. Particularly, one of the movable deflection points is comprised by the first loop of the suspension loop, the other movable deflection point is comprised by the second loop of the suspension loop (see also below).

Particularly, when the first pulling section is pulled the suspension loop will be shortened. When the first pulling section is released, then the implant (e.g. graft) or tissue connected to the suspension loop will apply the load on the suspension loop. This load will be transferred to the first pulling section in a loosening direction, which corresponds to a loosening force.

Because of the proportionally relation (moveable and fixed deflection points), the loosening force on the pulling section is e.g. divided by four, which is relatively low and allows locking of the first pulling section by the (overhead) locking loop.

Furthermore, according to an embodiment of the implantable suspension device, the suspension plate comprises a front side and a rear side, which rear side faces away from the front side.

Furthermore, according to an embodiment of the implantable suspension device, said suspension plate comprises a plurality of through-holes, wherein the respective through-hole extends from the front side to the rear side of said suspension plate, wherein said suture element is configured to extend through said through-holes for engaging with the suspension plate.

Further, according to an embodiment of the suspension device according to the present invention, said plurality of through-holes is formed by at least or exactly six through-holes. Particularly, each through-hole can comprise a circular cross section.

Particularly, the stopper comprises a diameter that is larger than the diameter of a remaining portion of the suture element. Particularly, the diameter of the stopper is larger than a diameter of a first through-hole of said plurality of through-holes, through which first through-hole the suture element is initially inserted with the first end section ahead.

Furthermore, according to an embodiment of the suspension device, the suture element is inserted into said first through-hole of said plurality of through-holes with the first end section ahead such that the stopper butts against the suspension plate (particularly against the front side and/or an inner wall of the first through-hole) to prevent the suture element from being completely pulled through the first through-hole of the suspension plate.

Furthermore, according to an embodiment of the suspension device, the suture element is furthermore successively inserted into a second through hole, a third-through hole, a fourth through-hole and fifth through-hole of said plurality of through-holes such that said adjustable suspension loop is formed extending from the front side of the suspension plate and/or such that a locking loop is formed on the rear side of the suspension plate, wherein the first end section of the suture element is further inserted into the locking loop for clamping the first end section of the suture element by means of the locking loop to the rear side of the suspension plate with a locking force.

Furthermore, according to an embodiment of the suspension device, the suspension loop comprises a first loop and a second loop formed by the suture element, wherein particularly according to an embodiment said two loops extend along one another.

Furthermore, according to an embodiment of the suspension device, the suture element is inserted such into said first to fifth through-holes that a pulling force applied to first end section of the suture element and transferred to the suspension loop is amplified by a factor of at least four, and/or particularly such that said locking force is a friction force with a pressing force at least twice as large as said pulling force on the first pulling section of the suture element.

Furthermore, according to an embodiment of the suspension device, said plurality of through-holes comprises a second through-hole, wherein the suture element is inserted into the second through-hole, particularly from the rear side of the suspension plate with the first end section ahead, so that the locking loop is formed on the rear side of the suspension plate.

Furthermore, according to an embodiment of the suspension device, said plurality of through-holes comprises a third through-hole, wherein the suture element is inserted into the third through-hole, particularly from the front side of the suspension plate with the first end section ahead, so that the first loop of the suspension loop is formed on the front side of the suspension plate.

Furthermore, according to an embodiment of the suspension device, said plurality of through-holes comprises a fourth through-hole, wherein the suture element is inserted into the third through-hole, particularly from the rear side of the suspension plate with the first end section ahead.

Furthermore, according to an embodiment of the suspension device, said plurality of through-holes comprises a fifth through-hole, wherein the suture element is inserted into the fifth through-hole, particularly from the front side of the suspension plate with the first end section ahead, so that the second loop of the suspension loop is formed on the front side of the suspension plate.

Furthermore, according to an embodiment of the suspension device, said first end section protruding out of the fifth through-hole is inserted into said locking loop, wherein a portion of said first end section of the suture element protruding out of the locking loop forms a first pulling section of the suture element for pulling on the suture element so as to shorten/tighten the suspension loop Furthermore, according to an embodiment of the suspension device, the suspension device comprises a sixth through hole, wherein said first end section protruding out of the locking loop is insertable into said sixth through hole, particularly from the rear side of the suspension plate, to form a second and a third pulling section (out of the first end section) extending from the sixth through hole, respectively, for pulling the suspension device through a bone tunnel.

Furthermore, according to an embodiment of the suspension device, the first, second, third and fourth through-holes are arranged on the corners of a (virtual) quadrangle, particularly square. Further, particularly, the first, second, third and fourth through-hole are further arranged between the fifths and the sixths through-hole. Further, particularly, the fifth through-hole faces the sixth through-hole in the direction of a longitudinal axis of the suspension plate. Further, particularly, the first through-hole and the second through-hole are arranged adjacent the fifth through hole. Further, particularly, the first through-hole faces the second through-hole in a direction perpendicular to the longitudinal axis. Further, particularly, the first through-hole faces the third through-hole in the direction of the longitudinal axis. Furthermore, particularly, the fourth through-hole is arranged diagonally to the first through-hole.

Furthermore, according to an embodiment of the suspension device, the sixth through hole has a larger opening area than the first to fifth through hole.

Furthermore, according to an embodiment of the suspension device, the stopper comprises at least one knot formed in the second end section of the suture element.

Furthermore, according to an embodiment of the suspension device, the stopper comprises a portion of the suture element arranged adjacent the at least one knot, which portion is formed out of merged fibers of the suture element. Particularly, the fibers are merged by heating and at least partially melting them.

Furthermore, according to an embodiment of the suspension device, the suspension device comprises an adapter plate, wherein the adapter plate comprises a recess for receiving the suspension plate in a form fitting manner. Particularly, the adapter plate can be made of other materials, such as biocompatible polymers like PEEK, PLA, etc., or biocompatible ceramics like HA, TCP, etc. According to yet a further embodiment of the suspension device, the suspension device comprises a plate member, wherein the plate member comprises recesses through which the suspension loop extends. Such an embodiment can be used to connect a bone to the suspension plate that rests on another bone, or to apply tension to a bone on which both the suspension plate and the plate member rest. Particularly, the function of this is to keep the tension of two pieces of bone, e.g. to compensate the force of the injured ligament, or to correct the position of the fractured bone or two bones, or to compensate the force of the injured ligament.

Furthermore, according to an alternative embodiment of the suspension device, the suspension device comprises a first plate member, wherein the first plate member comprises recesses through which the first loop of the suspension loop extends, and wherein the suspension device comprises a second plate member, wherein the second plate member comprises recesses through which the second loop of the suspension loop extends. Such an embodiment can be also be used to connect a bone to the suspension plate that rests an another bone, particularly to keep the tension of two bones, e.g. to compensate the force of the injured ligament.

According to a further aspect of the present invention, a tool for use with an implantable medical suspension device, particularly for use with an implantable medical suspension device according to the present invention, is disclosed, wherein the tool comprises:
  a handle for holding the tool
  a guide bar extending from said handle,
    at least a first slot formed into said guide bar (and particularly also into the handle) for receiving the suture element, and
  a distance probe slidably arranged in the guide bar.

Particularly, the tool can also be comprised by the suspension device according to the present invention, e.g., the suspension device comprises the tool as a separate component. Such a suspension device kit offers the benefit that the user also has a dedicated tool that helps arranging the suspension plate, suture element, and particularly implant, in the desired position (e.g. in a bone tunnel) and to adjust (e.g. tighten) the suspension loop.

Particularly, according to an embodiment of the tool comprises a second slot extending parallel to the first slot and formed into said guide bar (and particularly also into the handle) for receiving the suture element.

Furthermore, according to an embodiment of the tool according to the present invention, the tool is configured to clamp the suture element (particularly the first pulling section) in the first slot, and/or wherein the tool is configured to clamp the suture element (particularly the second and the third pulling section) in the second slot.

Furthermore, according to an embodiment of the tool, the tool comprises a first actuating element that can be actuated to clamp the first pulling section of the suture element in the first slot, and/or wherein the tool comprises a second actuating element that can be actuated to clamp the second and the third pulling section of the suture element in the second slot. Particularly, the two actuating elements are arranged on the handle, particularly on opposite sides of the handle.

Furthermore, according to an embodiment of the tool, the tool comprises a force indicator for (e.g. optically) indicating a pulling force to the user exerted onto the suture element, particularly on the first pulling section, via the tool.

Furthermore, according to an embodiment of the tool, the tool comprises a distance indicator for (e.g. optically) indicating a distance measured with the distance probe.

Particularly, the force indicator and/or the distance indicator are arranged on the guide bar.

Furthermore, according to an alternative embodiment of the tool according to the present invention, the distance probe comprises a handle at an end of the distance probe for moving the distance probe with respect to the guide bar (e.g. into the bone tunnel).

Further, according to an embodiment, the distance probe is configured to contact a suspension plate of the suspension device located in the bone tunnel so as to provide a user feedback about a current position of the suspension plate in the bone tunnel.

This is a very advantageous feature since it allows the user/surgeon to flip the suspension plate in a more controlled way to avoid the risk of the soft-tissue bridge. Particularly, this feature allows the user to place the suspension plate directly outside the bone tunnel on the bone surface without excessively clamping soft tissue between the suspension plate and bone surface.

According to a further embodiment of the tool, the tool comprises a rotatable distance measuring wheel configured to measure a displacement of the suture element with respect to the tool.

Further, according to an embodiment of the tool according to the present invention, the tool comprises a force indicator that is configured to receive and indicate a force exerted by the suture element, when the distance probe handle is moved to tension the suture element.

Furthermore, according to an embodiment of the tool, the distance measuring wheel and the force indicator are mounted to the guide bar such that the suture element is laced between the distance measuring wheel and the force indicator when received in the first slot.

Further, according to an embodiment of the tool, the tool comprises a self-locking clamp for clamping the suture element when the suture element is received in the first slot.

According to a further aspect of the present invention, an implantable suspension plate is disclosed (particularly for use with a single suture element) comprising a front side and a rear side facing away from the front side, wherein the suspension plate comprises six through-holes, wherein each through-hole extends from the front side to the rear side, and wherein the first, second, third and fourth through holes are arranged on the corners of a square, the first, second, third and fourth through holes being further arranged between the fifth and sixth through holes, the fifth through hole facing the sixth through hole in the direction of a longitudinal axis of the suspension plate, and the first through hole and the second through hole being arranged adjacent the fifth through hole, and the first through hole facing the second through hole in a direction perpendicular to the longitudinal axis and the third through hole in the direction of the longitudinal axis, while the fourth through hole is arranged diagonally to the first through hole.

Furthermore, according to an embodiment of the suspension plate according to the present invention, the sixth through hole has a larger opening area than the first to fifth through hole.

According to a further aspect of the present invention, a method for building an implantable suspension device (particularly according to the present invention) is disclosed, the method comprising the steps of:

providing a suspension plate comprising a front side for butting against a surface of a bone of a patient and a rear side, which rear side faces away from the front side, and wherein said suspension plate comprises six through-holes, which through-holes extend from the front side to the rear side of said suspension plate, providing a single elongated and flexible suture element comprising a free first end section and a second end section, and providing a stopper on the second end section.

Particularly, providing the stopper on the second end section of the suture element may further comprise the step of forming at least one knot in the second end section of the suture element.

Furthermore, alternatively, forming the stopper on the second end section of the suture element may further comprise the step of forming a portion of merged fibers of the suture element, wherein afterwards at least one knot is formed adjacent said portion.

Further, particularly, the method for forming the stopper disclosed below can also be used for forming the stopper.

Furthermore, according to an embodiment of the method according to the present invention, the method further comprises the step of inserting the suture element into a first through-hole of said six through-holes with the first end section ahead such that the stopper butts against the suspension plate (particularly against the front side of the suspension plate and/or an inner wall of the first through-hole) to prevent the suture element from being completely pulled through the first through-hole of the suspension plate.

Furthermore, according to an embodiment of the method, the method further comprises the step of inserting the suture element into a second through-hole of said six through-holes, particularly from the rear side of the suspension plate with the first end section ahead, so that a locking loop is formed on the rear side of the suspension plate.

Furthermore, according to an embodiment of the method, the method further comprises the step of inserting the suture element into a third through-hole of said six through-holes, particularly from the front side of the suspension plate with the first end section ahead, so that a first loop is formed on the front side of the suspension plate.

Furthermore, according to an embodiment of the method, the method further comprises the step of inserting the suture element into a fourth through-hole of said six through holes, wherein the suture element is inserted into the fourth through-hole, particularly from the rear side of the suspension plate, with the first end section ahead.

Furthermore, according to an embodiment of the method, the method further comprises the step of inserting the suture element into a fifth through-hole of said six through-holes, wherein the suture element is inserted into the fifth through-hole, particularly from the front side of the suspension plate with the first end section ahead, so that a second loop is formed on the front side of the suspension plate, which second loop forms a suspension loop together with the first loop on the front side of the suspension plate.

Furthermore, according to an embodiment of the method, the method further comprises the step of inserting said first end section protruding out of the fifth through-hole into said locking loop so that a portion of said first end section of the suture element protruding out of the locking loop forms a first pulling section of the suture element for pulling on the suture element so as to shorten/tighten the suspension loop.

Furthermore, according to an embodiment of the method, the method further comprises the comprises the step of inserting said first end section of the suture element protruding out of the locking loop into a sixth through hole of said six through-holes, particularly from the rear side of the suspension plate, to form a second and a third pulling section extending from the sixth through hole, respectively, for pulling the suspension device through a bone tunnel.

According to yet another aspect of the present invention, a method for forming a stopper on an end section of a suture element is disclosed, wherein the method comprises the steps of:

providing a suture element having a first and a second end section, forming a portion of merged fibers of the suture element by merging heated individual fibers of the suture element at the second end section, forming at least one knot adjacent said portion of merged fibers, inserting the suture element with the first end section ahead into a through-hole of a plate, and pressing said at least one knot towards said portion of merged fibers by pulling on the first end section of the suture element so that the knot is pressed against a surface of the plate delimiting said through-hole.

Figure 2:
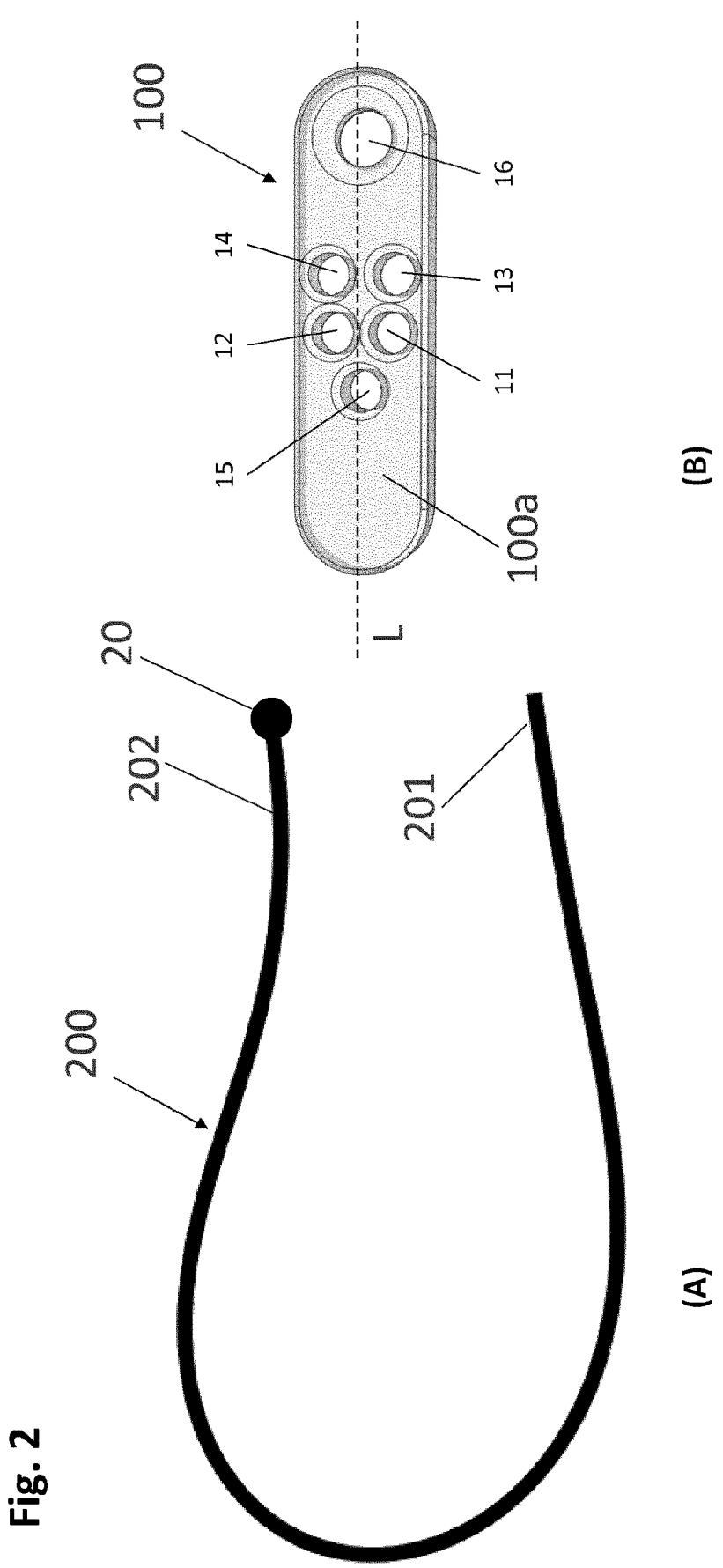
Figure 3:
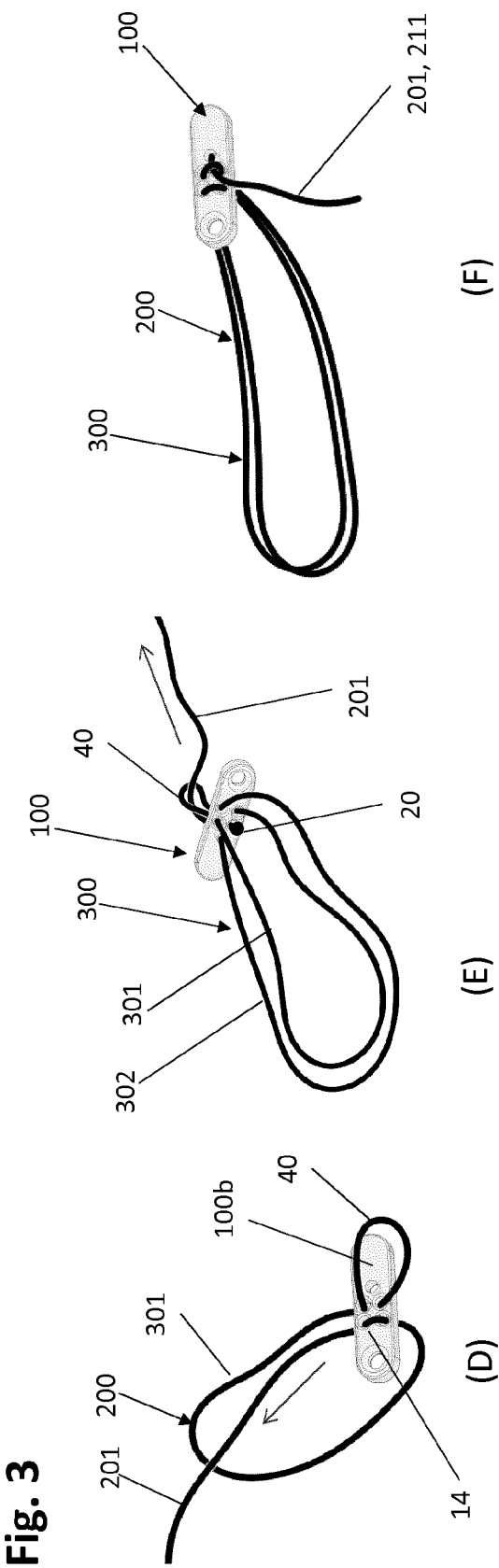
Figure 4:
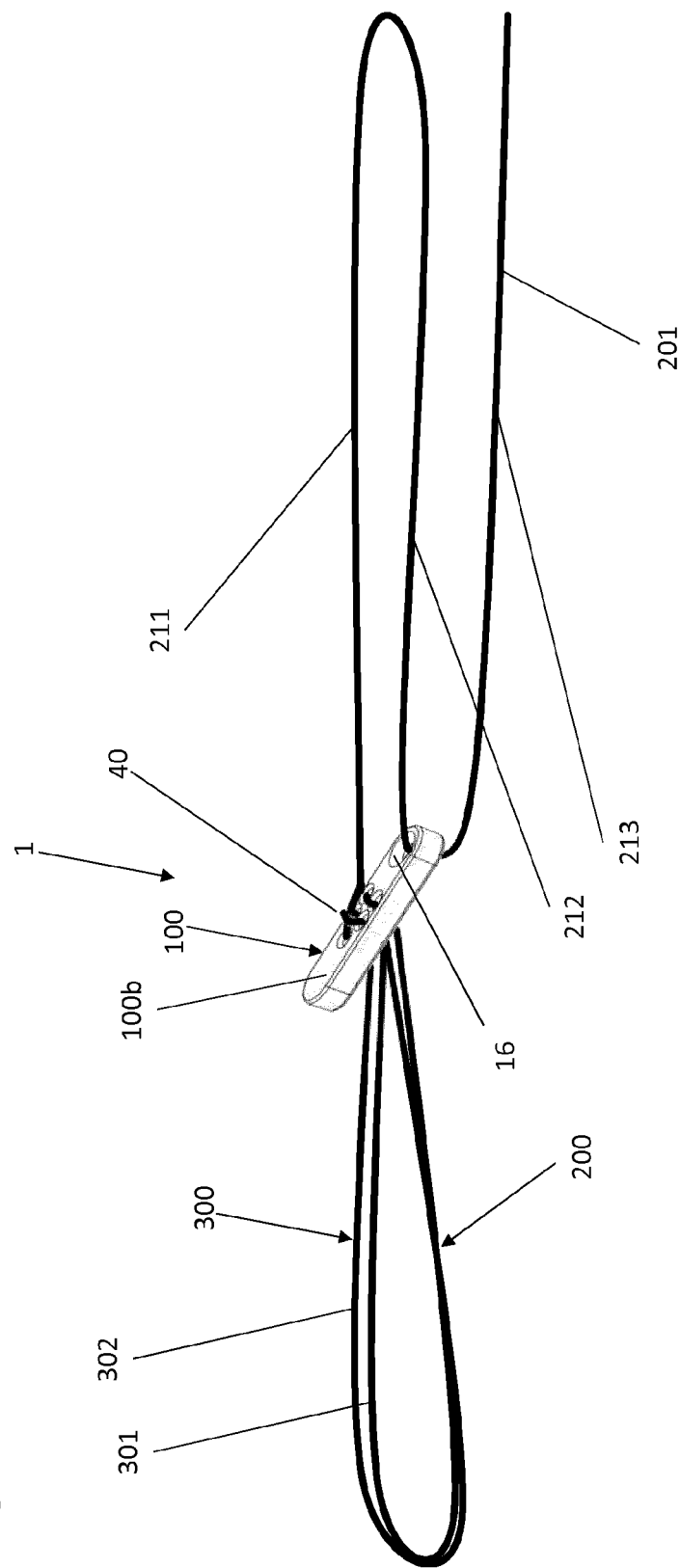
Figure 5:
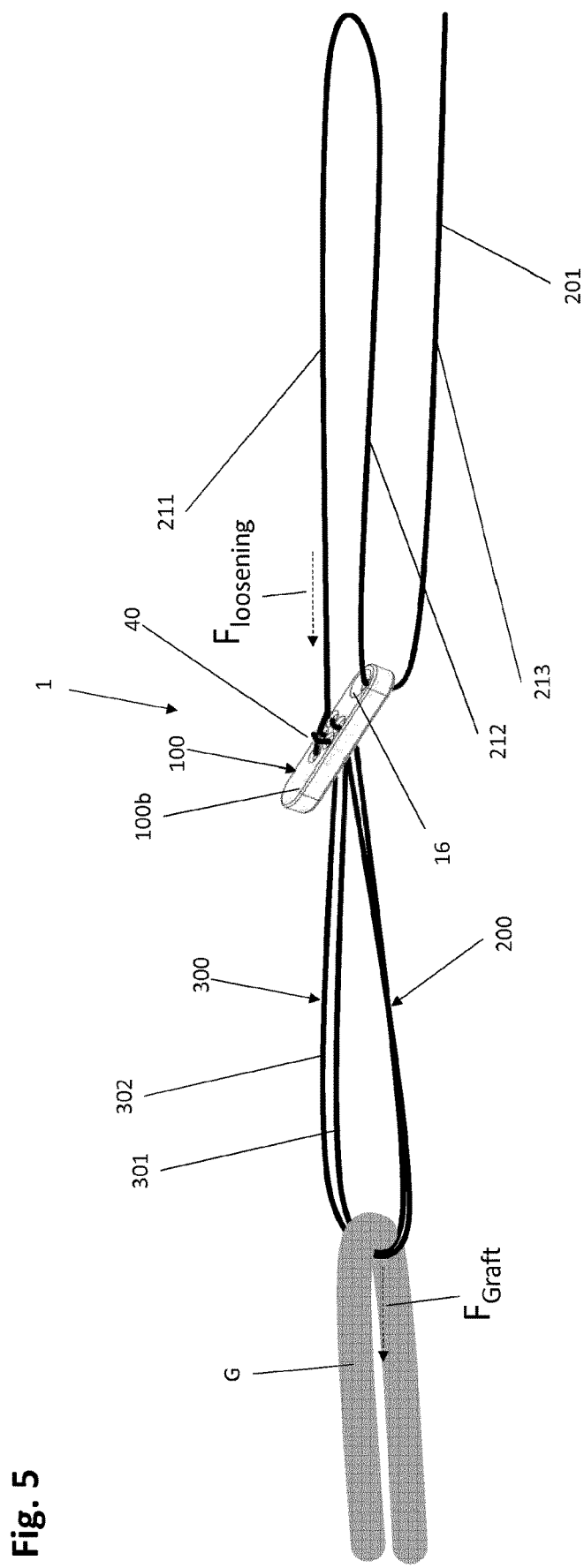
Figure 6:
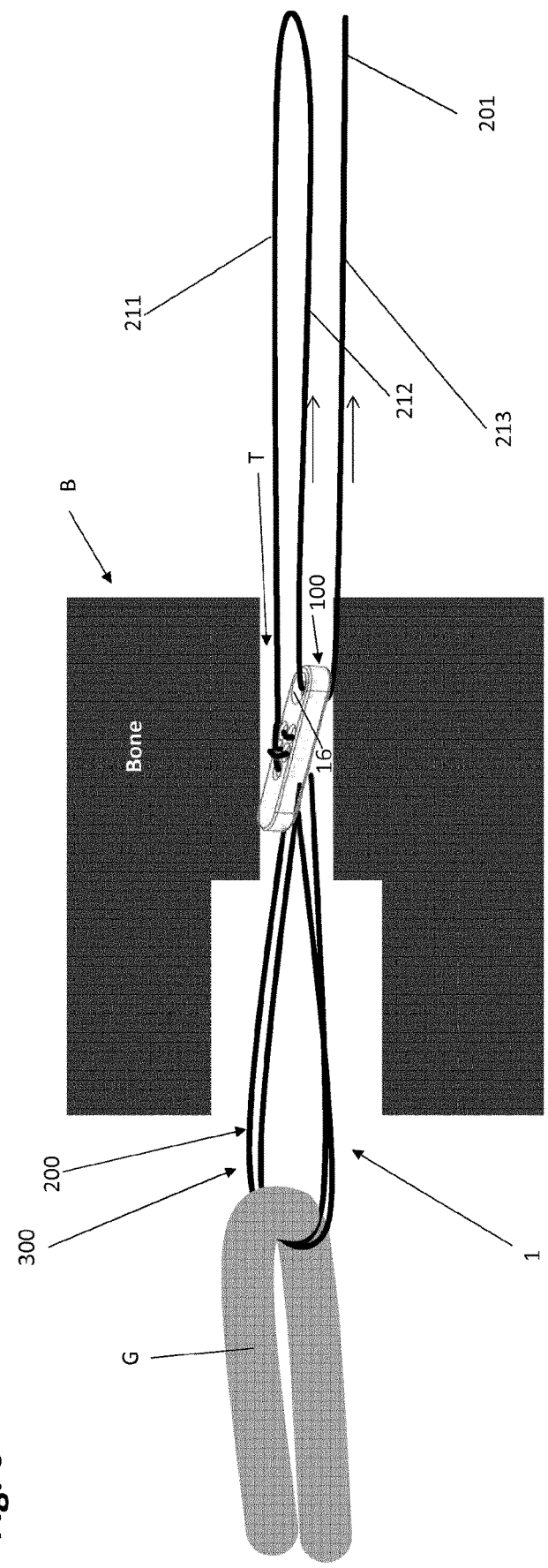
Figure 7:
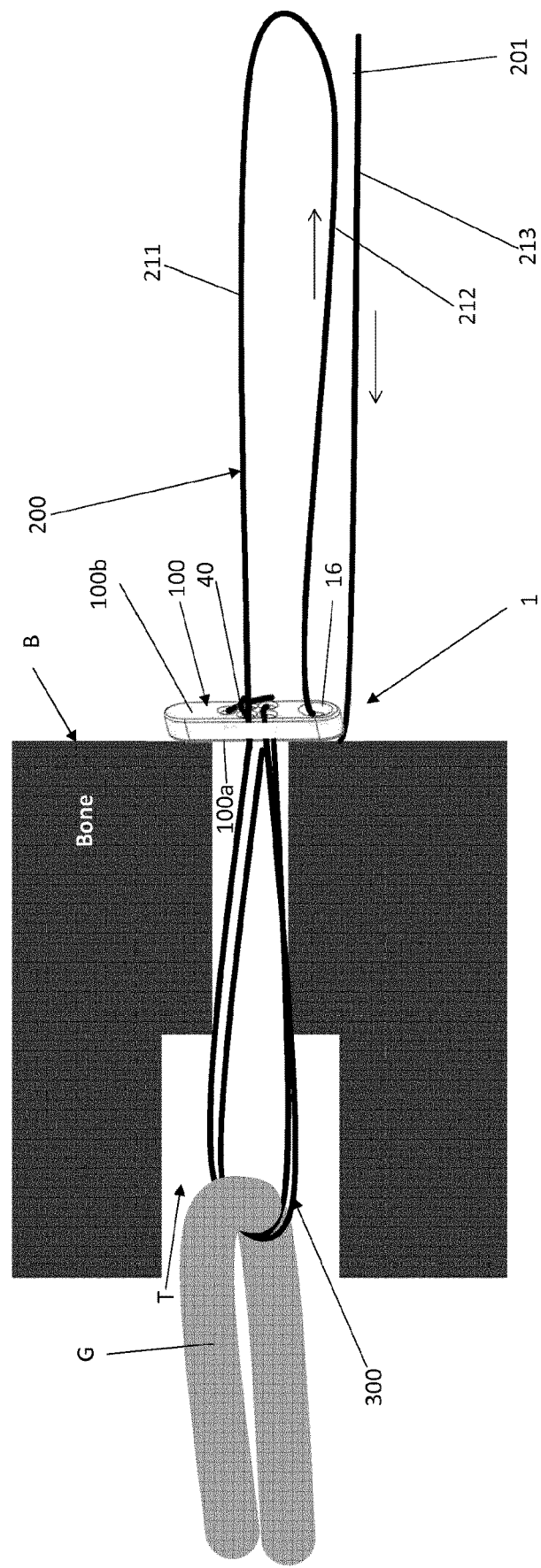
Figure 8:
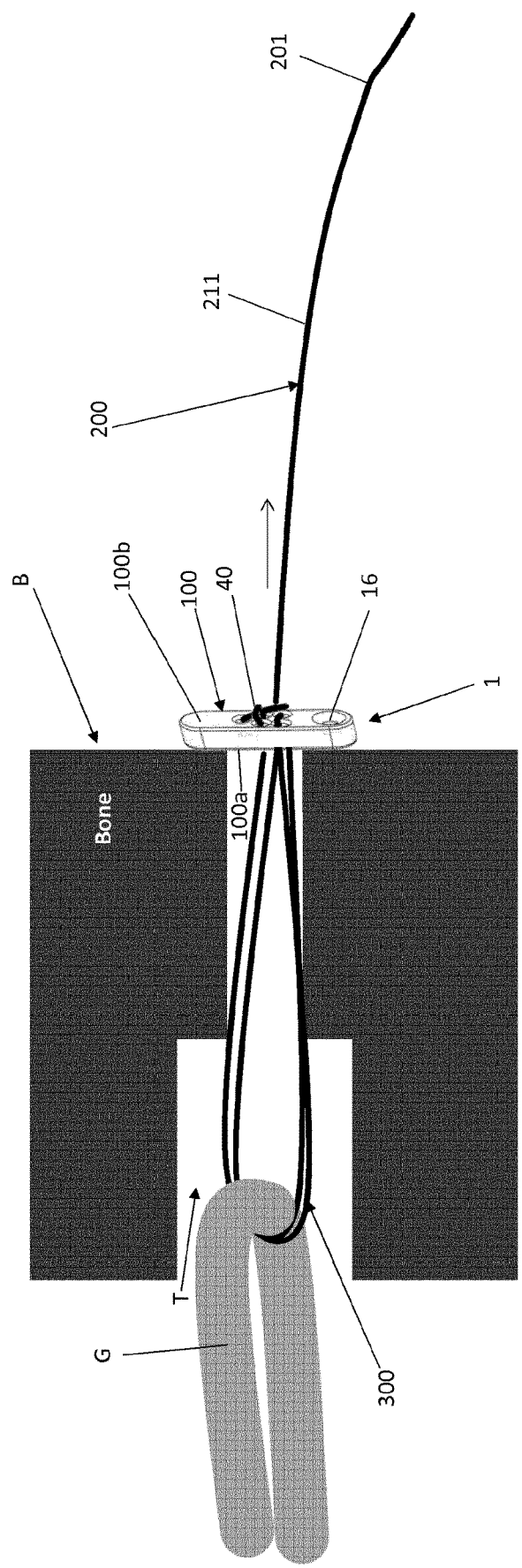
Figure 9:
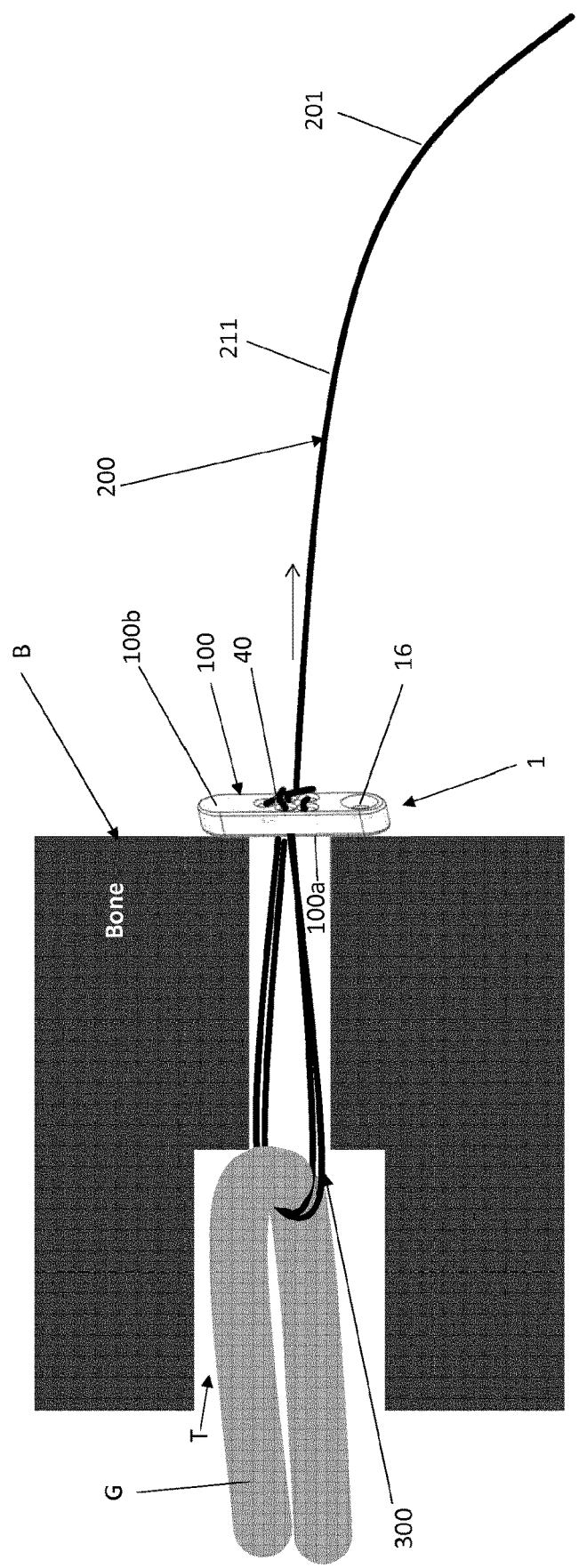
Figure 10:
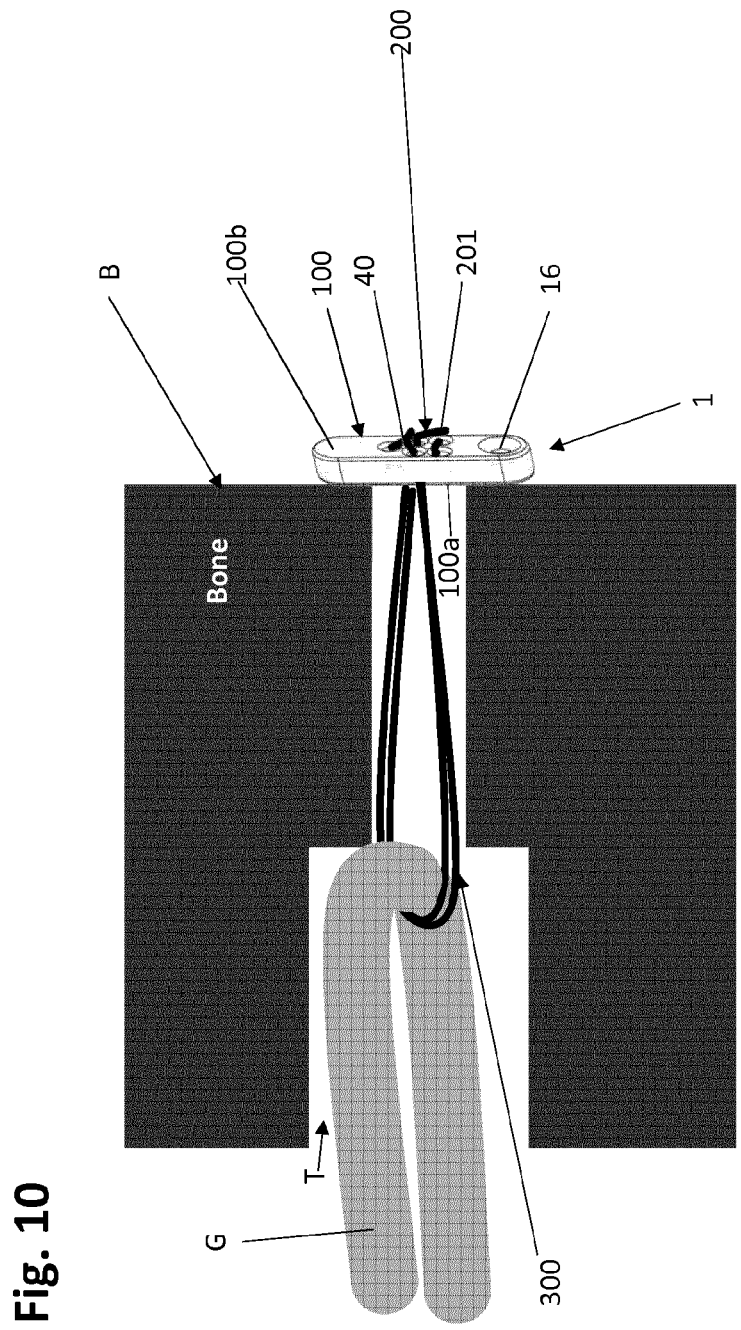
Figure 11:
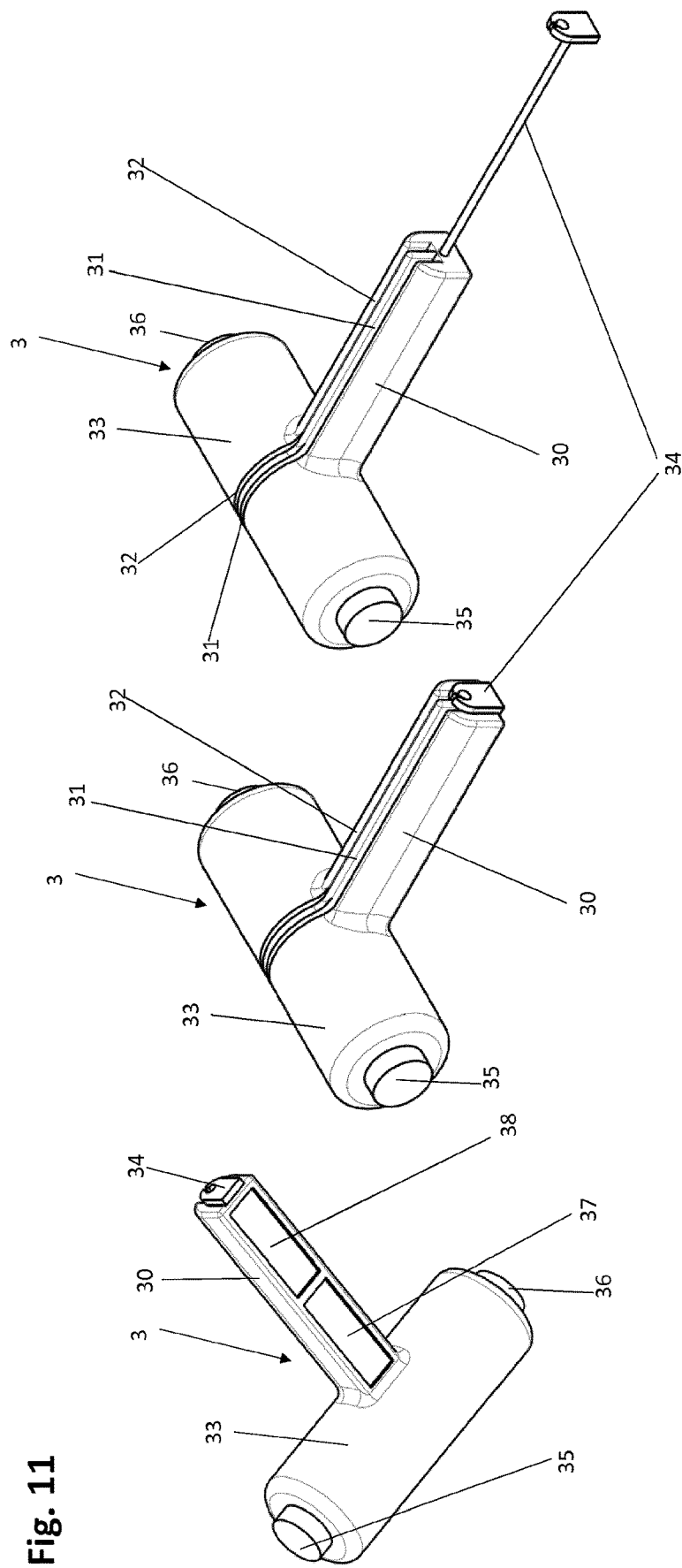
Figure 14:
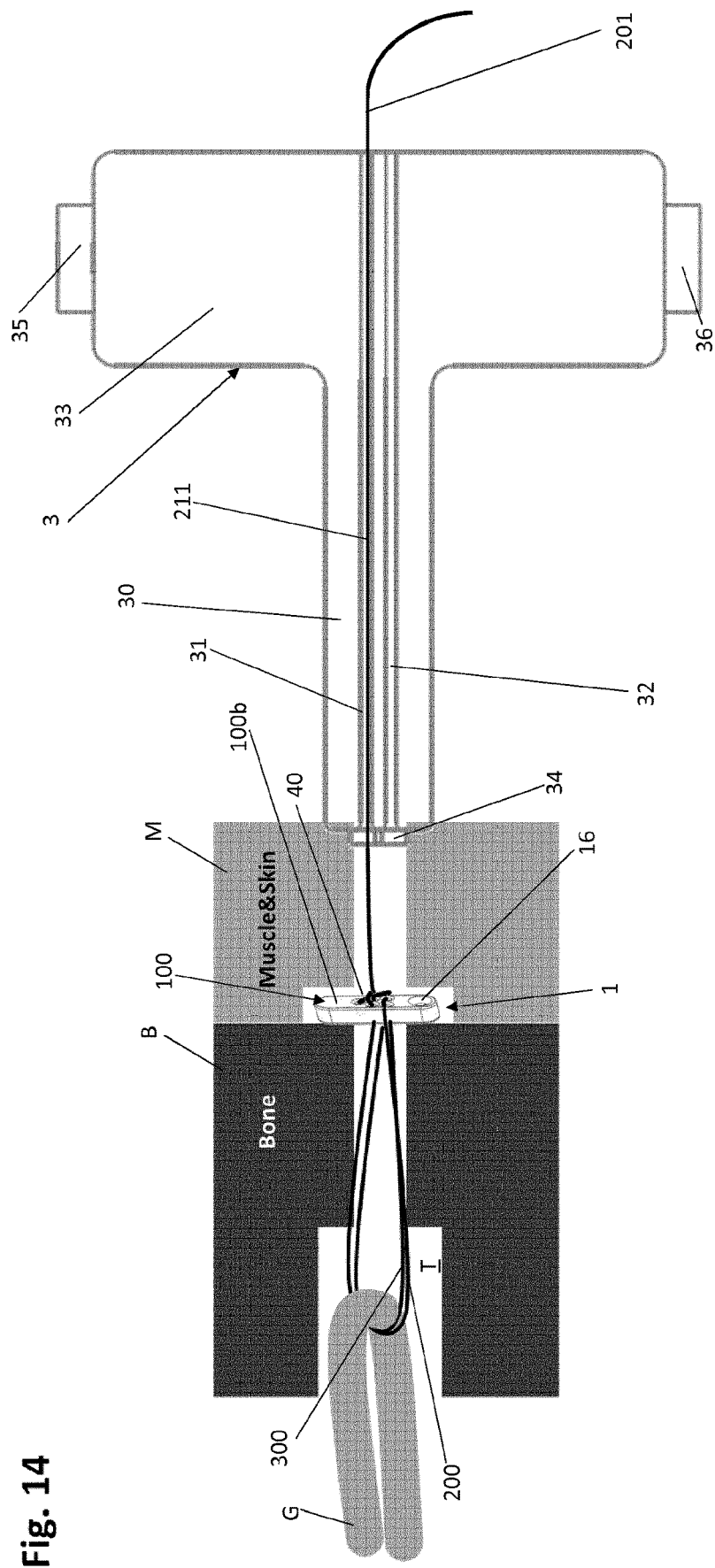
Figure 15:
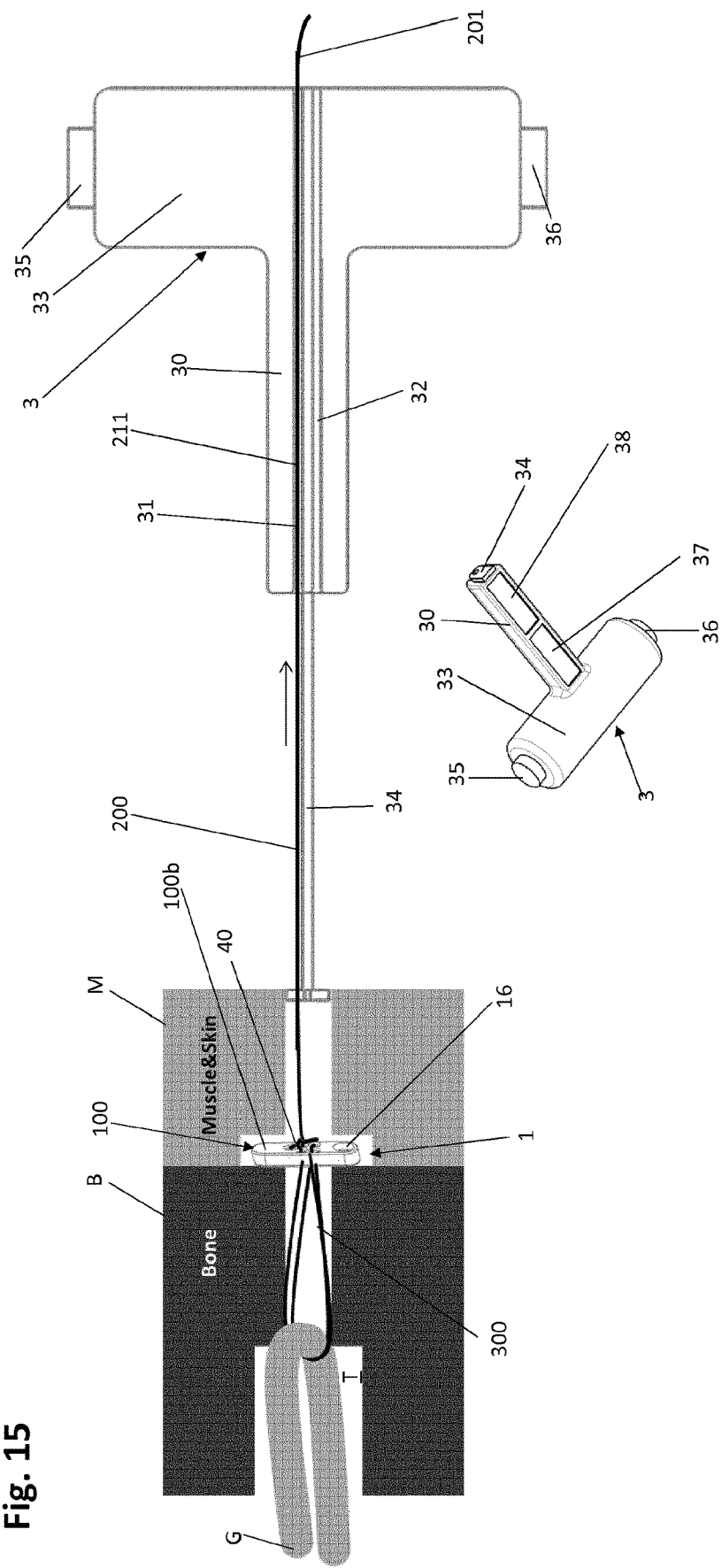
Figure 16:
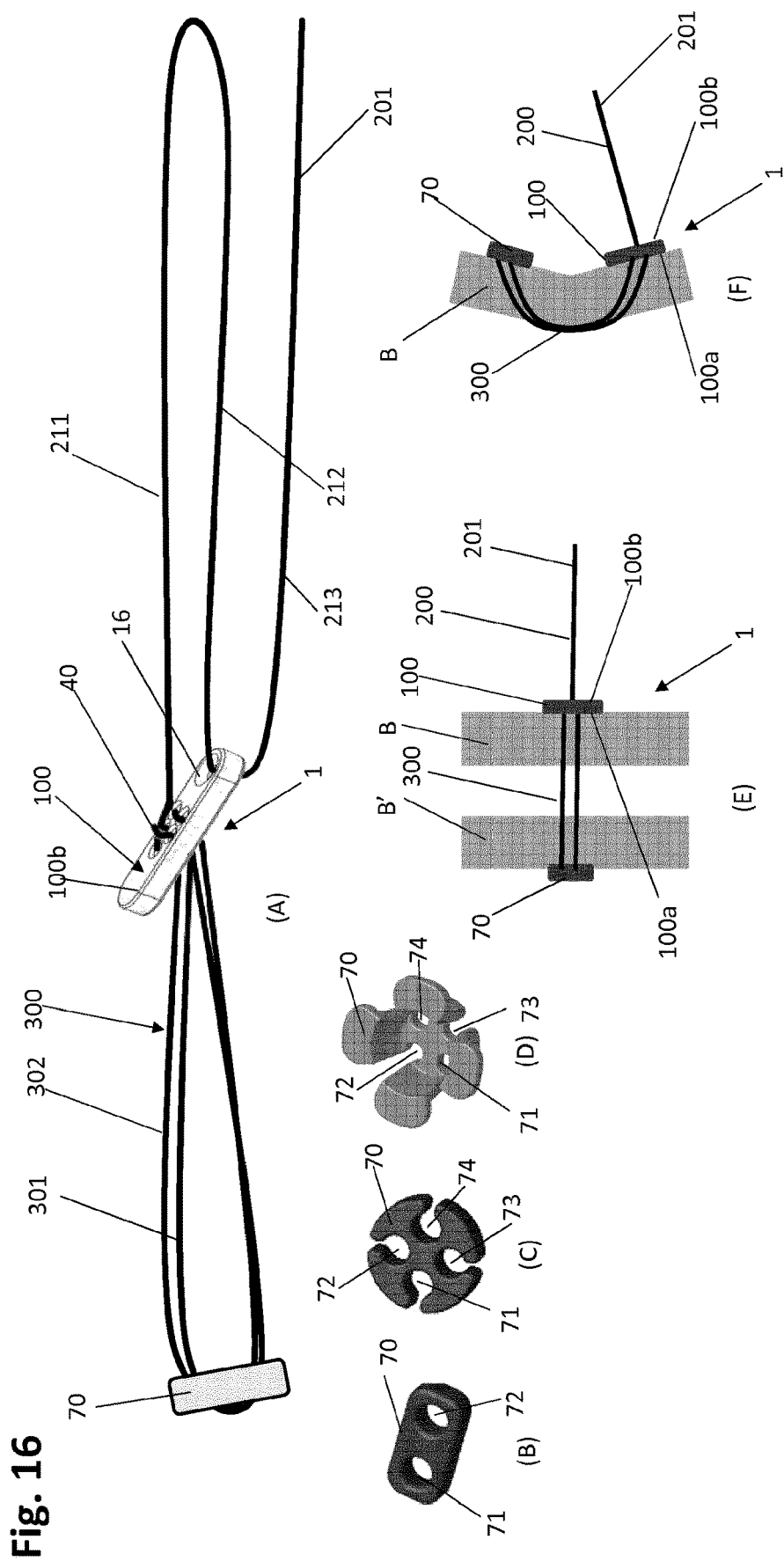
Figure 17:
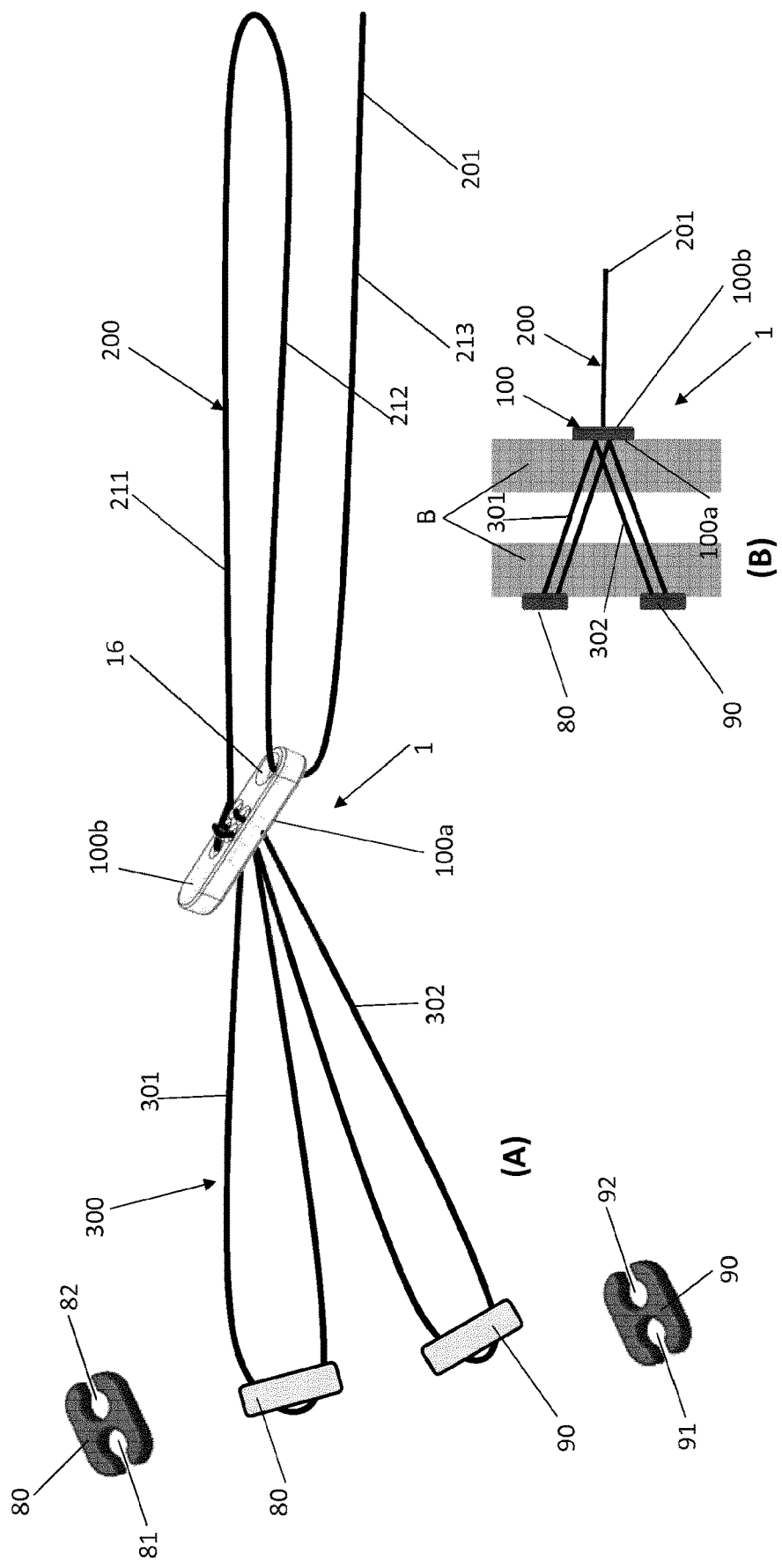
Figure 18:
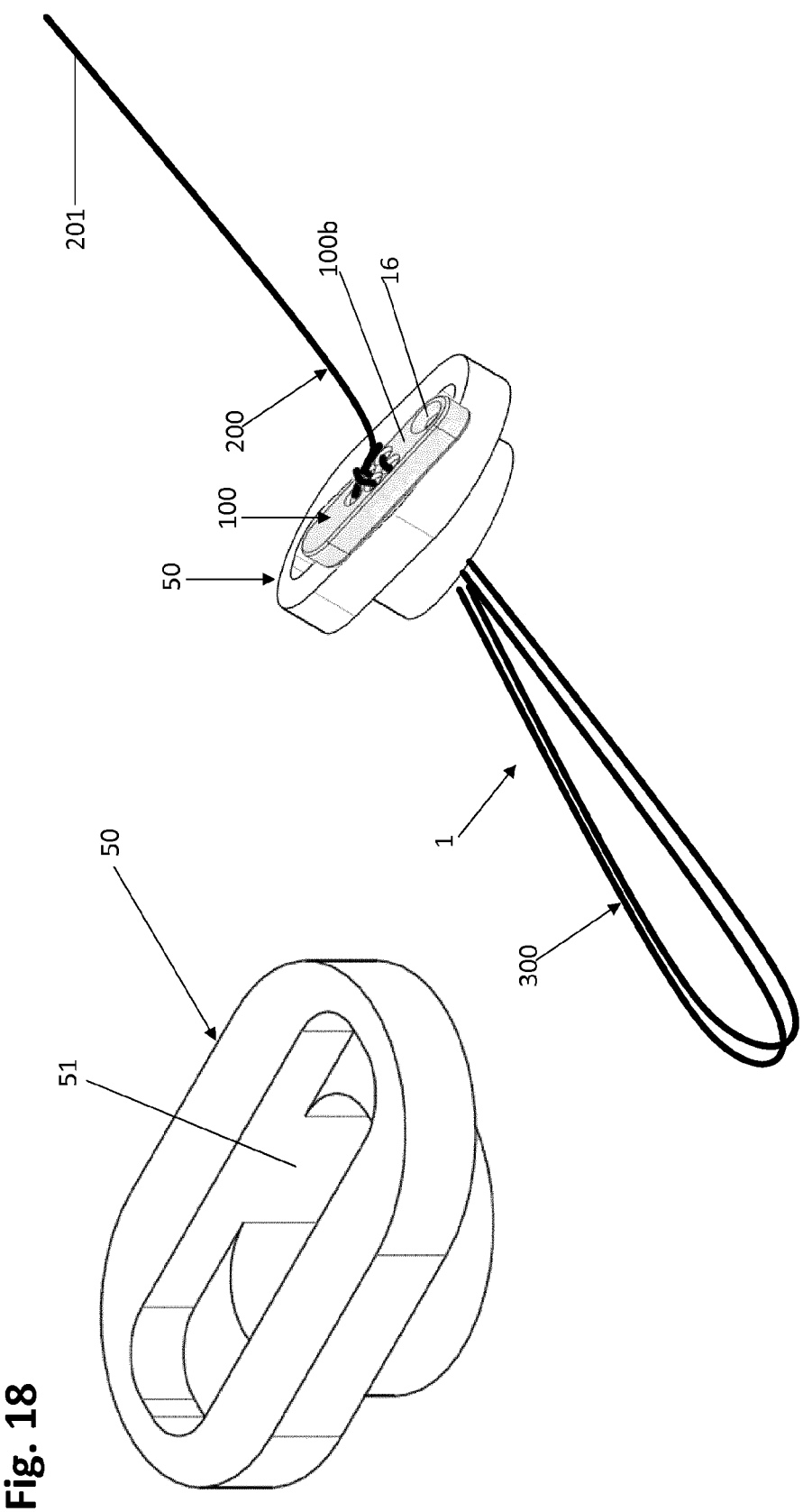
Figure 19:
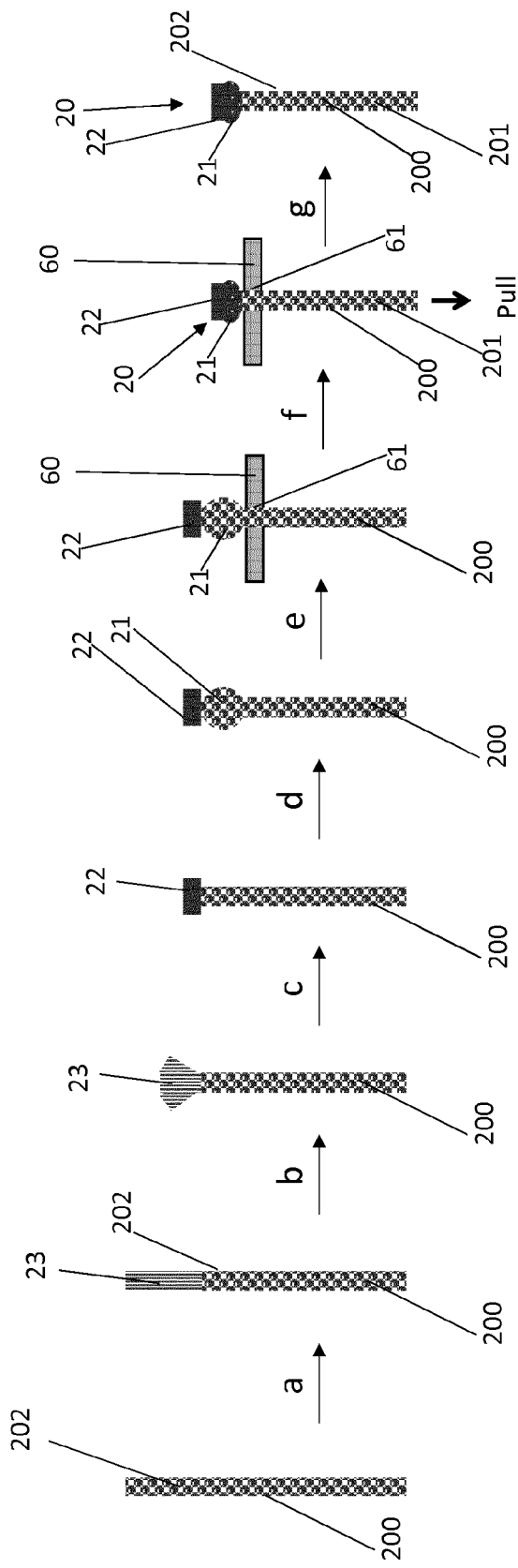

Further features and advantages of the invention shall be described by means of detailed descriptions of embodiments with reference to the Figures, wherein FIG. 1 shows the working principle (B) of an embodiment of an implantable suspension device according to the present invention shown in (A), FIG. 2 shows the components of an embodiment of an implantable suspension device according to the present invention, namely a single suture element (A), and a suspension plate (B), FIG. 3 shows the step of building the embodiment of the suspension device shown in FIG. 4 by mounting the suture element to the suspension plate, FIG. 4 shows an embodiment of an implantable suspension device according to the present invention, FIG. 5 shows connecting an implant, particularly in the form of a graft, to the suspension loop of the suspension device shown in FIG. 4, FIG. 6 shows inserting the suspension device of FIG. 5 into a bone tunnel, FIG. 7 shows remove of the second and third pulling section of the suture element from the sixth through-hole of the suspension plate of the suspension device of FIG. 5, FIG. 8 shows shortening of the suspension loop of the suspension device of FIG. 5 by means of the first pulling section of the suture element, FIG. 9 shows bringing the implant (e.g. graft) into a desired position using the first pulling section shown in FIG. 8, FIG. 10 shows cutting off the first pulling section from the suture element after positioning of the implant, FIG. 11 shows different views of an embodiment of a tool according the present invention, which tool is configured for pulling the pulling sections of the suture element with a controllable force and distance, FIGS. 12-15 shows positioning of the implant using the tool shown in FIG. 11, FIG. 16 shows a further embodiment of a suspension device according to the present invention for connecting two bones to one another or for applying tension to a bone, FIG. 17 shows a further embodiment of a suspension device according to the present invention for connecting two bones to one another, FIG. 18 shows an adapter plate for the suspension plate, and FIG. 19 shows an embodiment of a method for forming a stopper on a second end section of a suture element.

Figure 20:
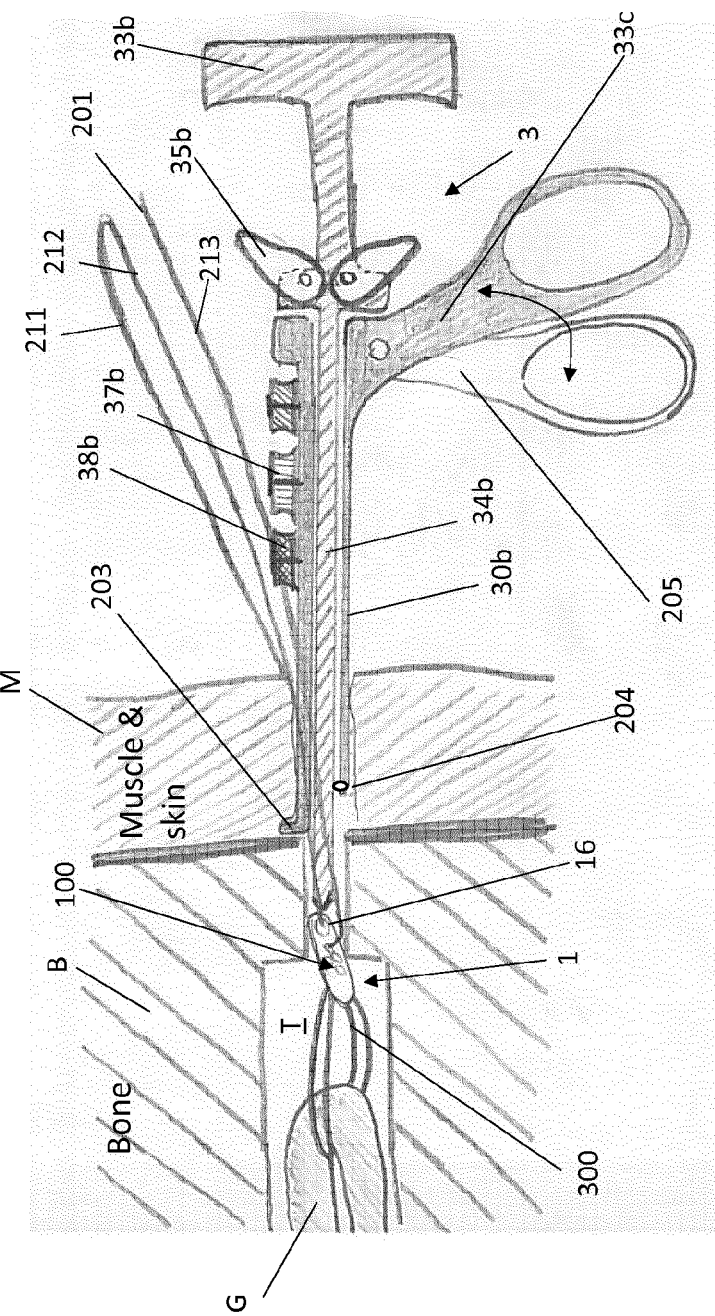
Figure 21:
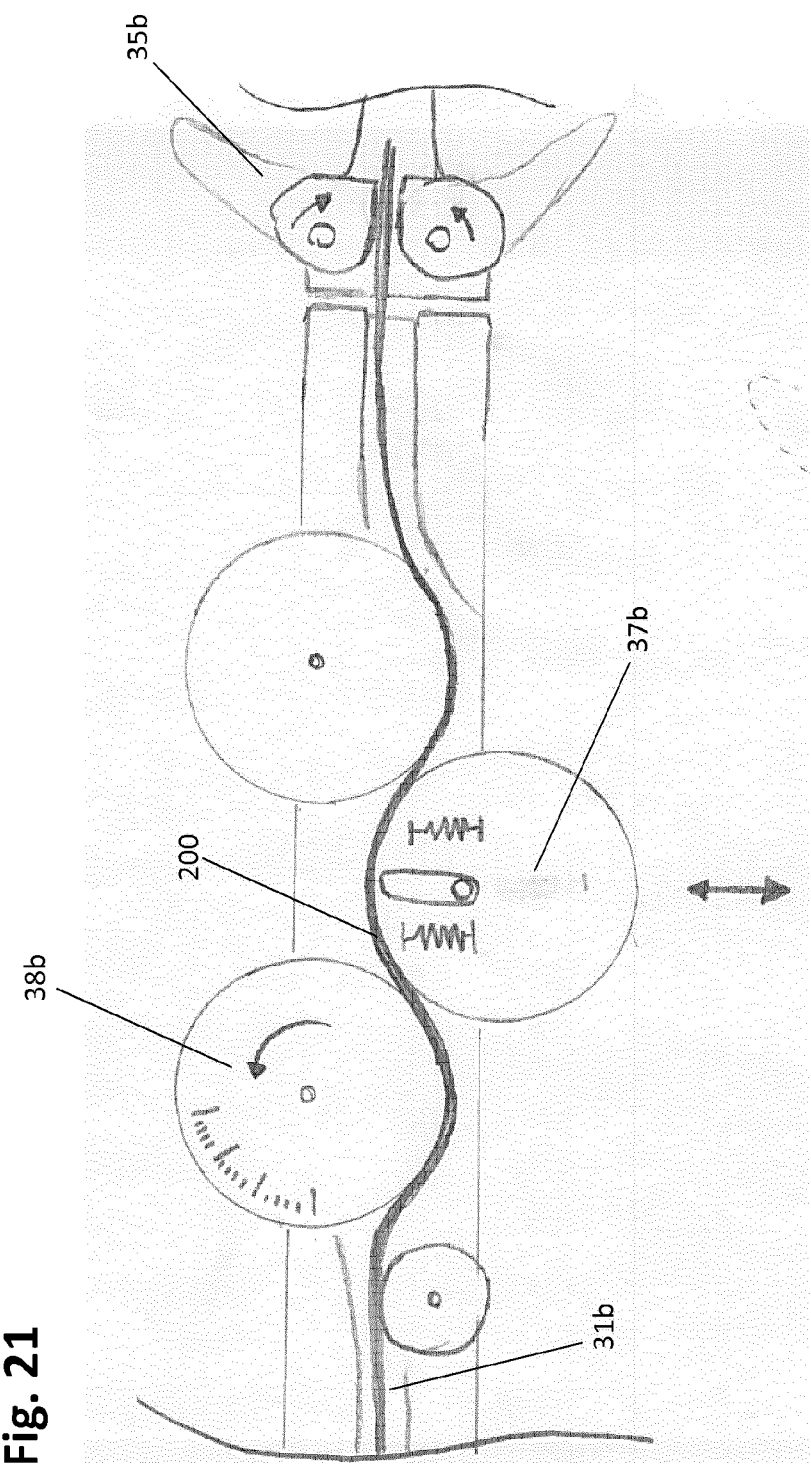
Figure 22:
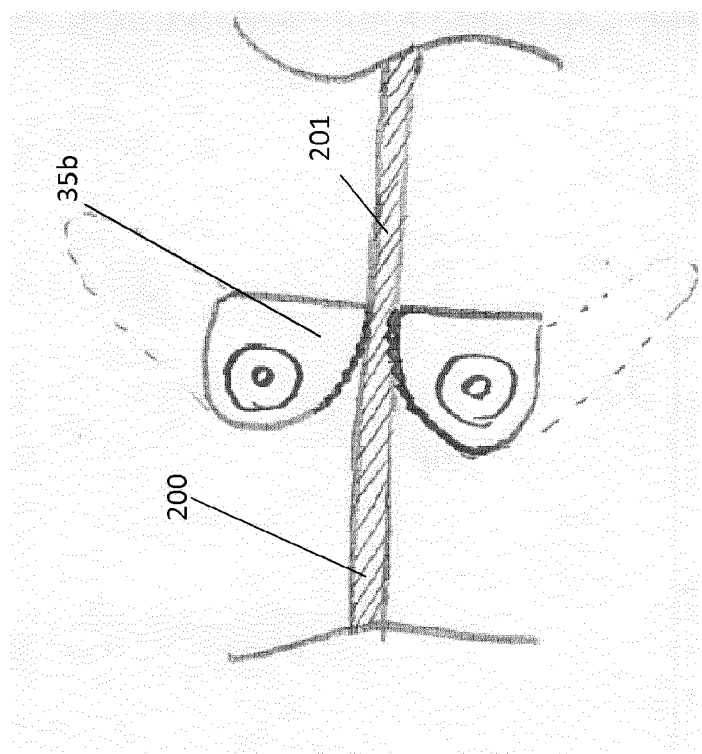

FIGS. 20-22 show an alternative embodiment of the tool according to the present invention;

Particularly, according to an embodiment of a suspension device 1 according to the present invention as shown in FIG. 1 (A) comprises a suspension mechanism having a locking mechanism that is based on the reduction force of movable deflection points (schematically illustrated as pulleys in FIG. 1 (B)) with double force locking pressure on the free end section 201. Advantageously, according to an embodiment of the suspension device 1 according to the present invention, the latter comprises a one strand design, i.e., the device 1 particularly needs only one suture element 200. Here, the whole mechanism and procedure is achieved by only one suture element 200.

This leads to a better usability of the device 1, since only one strand (e.g. the first pulling section 211) needs to be pulled. The suspension device 1 according to the present invention is thus easier to use and the risk of a mis-use is considerably lower. The resulting design is more cost effective, as well as easier and faster to produce.

As shown in FIG. 1(A) an embodiment of the suspension device according to the present invention comprises a suture element 200 that has a first and a second end section, wherein the first end section is kept free and forms a pulling section and a stopper 20 is provided on the second end section.

As indicated in FIG. 1(A), the suture goes through the through-holes formed in a suspension plate 100 and is laid around the implant/tissue G so that the suspension loop 300 comprises two deflection points P (one on each loop 301, 302) movable with respect to the suspension plate 100 and a deflection point P' fixed with respect to the suspension plate 100. This mechanically corresponds to two movable pulleys P and one fixed pulley P', as shown in the schematical illustration of FIG. 1(B).

Because of the two movable pulleys P, the force F applied on the free pulling section 211 of the suture element 200 is amplified four times transferring to the suspension force applied on the graft G via the suspension loop 300 which comprises a first and a second loop 301, 302.

When releasing the free pulling section 211, the first free end section 201 is locked by the pressure with a locking loop 40. Particularly, the force on the locking loop 40 is twice as much as the force F on the free first end section 201.

Particularly, the locking force $F_L$ is transferred to the friction force. The loosening force $F_{loosening}$ (cf. also FIG. 5) equals the force on the first free end section 201 minus the system friction, which is mostly coming from the fixed pulley part P', i.e. from friction between the suture element 200 and corresponding through-holes of the suspension plate 100. Therefore, the self-locking mechanism can be described as follows:

Locking Force $F_L$(friction force with 2 F pressure)
>Loosening Force $F_{loosening}$(Force on free first end section 201($F$)−system friction force)

Generally, this mechanism can be generalized by adding loops (i.e. movable and fixed deflection points/pulleys) according to different indications. The more movable/fixed deflection points (pulleys), the higher the correlation ratio on the suspension force transferred from the pulling section 211.

The present invention thus differs significantly from known solutions in the prior art (see also above), where high friction is created by putting one suture through another suture's sleeve, or by using self-locking knots. In contrast thereto, the present invention particularly uses movable/fixed deflection points to reduce the loosening force on the free (first) pulling section 211, and particularly lock it with an overhead loop 40 pressed with double the force of loosening.

As indicated in FIG. 2, a suspension device 1 according to the present invention comprises two main components, one is an elongated and flexible (particularly pliable) suture element 200 shown in FIG. 2(A), and the other is a suspension plate 100 shown in FIG. 2(B).

Particularly, the suture element 200 has a free first end section 201 on the one side, and a stopper 20 on the other side, i.e. on a second end section 202.

Furthermore, in order to allow the suture element 200 to engage with the suspension plate 100, the latter comprises a plurality of through-holes 11, 12, 13, 14, 15, 16 that are organized in a way which enables to use said movable and fixed deflection points to reduce the loosening force.

Furthermore, the suspension plate 100 particularly has six through-holes 11, 12, 13, 14, 15, 16, particularly with smooth edges and surfaces, as shown in the FIG. 2(B).

Preferably, according to an embodiment, the six through-holes 11, 12, 13, 14, 15, 16 may be arranged in the following way.

Particularly, the suspension plate 100 comprises a front side 100a and a rear side 100b facing away from the front side 100a, wherein each through-hole 11, 12, 13, 14, 15, 16 extends from the front side 100a to the rear side 100b of the suspension plate 100. Particularly, the first, second, third and fourth through-holes 11, 12, 13, 14 are arranged on the corners of a virtual quadrangle, wherein the first, second, third and fourth through-holes 11, 12, 13, 14 are further arranged between the fifth and the sixth through-hole 15, 16, the fifth through-hole 15 facing the sixth through-hole 16 in the direction of a longitudinal axis L of the suspension plate (100), and the first through-hole 11 and the second through-hole 12 being arranged adjacent the fifth through-hole 15, and the first through-hole 11 facing the second through-hole 12 in a direction perpendicular to the longitudinal axis L and the third through-hole 13 in the direction of the longitudinal axis L, while the fourth through-hole 14 is arranged diagonally to the first through-hole 11.

In order to build the suspension device shown in FIG. 4, the following steps are particularly conducted to mount the suture element 200 to the suspension plate 100, as shown in FIG. 3:

Put the free first end section 201 of the suture element 200 through the first through-hole 11 of the suspension plate 200 until the stopper 20 touches the first through-hole 11 or surrounding surface of the front side 100a of the suspension plate 100 (cf. FIG. 3(A)).

Put the first end section 201 of the suture element 200 from the rear side 100b through the second through-hole 12 of the suspension plate 100, and leave a small locking loop 40 for a later step (cf. FIG. 3(B)).

Put the first end section 201 of the suture element 200 through the third through-hole 13 of the suspension plate 100, to form a first loop 301 of a final suspension loop 300 to be formed (cf. FIG. 3(C)).

Put the first end section 201 of the suture element 200 back through the fourth through-hole 14 of the suspension plate (cf. FIG. 3(D)).

Put the first end section 201 of the suture element 200 through the fifth through-hole 15 of the suspension plate 100 to form the second loop 302 and therewith the combined suspension loop 300 (cf. FIG. 3(E)).

Put the first end section 201 of the suture element through the locking loop 40 (cf. also FIG. 3(B))), and shorten the locking loop 40, to form the single strand self-locking construct (cf. FIG. 3(F)).

Put the first end section 201 of the suture element 200 through the six through-hole 16 of the suspension plate 100 to form a second and a third pulling section 212, 213 of the suture element 200 (cf. FIG. 3(G)).

Particularly, the afore-mentioned assembly steps according to FIG. 3(A) to FIG. 3(G) are conducted outside the body of the patient, i.e., ex vivo.

An exemplary use of an embodiment of the suspension device 1 according to the present invention as shown in FIG. 4 is illustrated in FIGS. 5 to 10.

As shown in FIG. 4 the device 1 comprises a first and a second loop 301, 302 forming the actual suspension loop 300, which loops 301, 302 are arranged on a front side 100a of the suspension plate 100. Further, there are three pulling sections 211, 212, 213 extending on the rear side 100b of the suspension plate 100, wherein a first pulling section 211 is configured for shortening the loops 301, 302 (i.e. the suspension loop 300), while the other two pulling sections 212, 213 are configured for pulling the suspension device 1 through a bone tunnel T.

The graft G (or some other implant or tissue) is enlaced into the suspension loop 300 as shown in FIG. 5, wherein particularly both loops 301, 300 extend along one another are laid around a periphery of the graft G.

Particularly, when the first pulling section 211 is released, the tension force applied on the graft G ($F_{graft}$) will be transferred to the pulling section 211 in the opposite direction of pulling, this force is defined as loosening force $F_{loosening}$.

When the first pulling section 211 is released, the loop 300 has a tendency of loosening/elongating because of the tension force of the graft G. The stronger the tension of the graft G, the higher the locking force on locking loop 40. This establishes the self-locking mechanism.

In order to bring the graft into the bone tunnel T, tension is kept on the graft G and the latter is pulled into the bone tunnel by pulling on the second and third pulling section 212, 213 as indicated by the arrows in FIG. 6. In this way the whole suspension device 1 with graft G is brought into the bone tunnel T.

When the suspension plate 100 is outside the bone tunnel T as shown in FIG. 7, the second and the third pulling section 212, 213 are removed from the suspension plate as indicated by the arrows while keeping the tension on the graft G.

Then, to shorten the loops 301, 302, the first pulling section 211 is pulled in the direction of the arrow indicated in FIG. 8. This is done until the graft G reaches the desired position, shown in FIG. 9. Finally, the pulling section 211 can be cut off from the suture element 200. The graft G is now securely suspended within the bone tunnel T, as shown in FIG. 10.

Advantageously the above procedure can be conducted using only a single suture element achieving the whole function, without additional pulling sutures.

Furthermore, for shortening the loops 301, 302 (i.e. the suspension loop 300), only one pulling section 211 needs to be pulled, without worrying to pull equal force/distance on several strands, which simplifies the use of such a device significantly.

Finally, the suture element 200 can be secured by means of the locking loop in a knotless fashion securely assured by the self-locking mechanism.

The above-mentioned steps of using/operating a suspension device 1 according to the present invention are fully functional without the tool 3 provided by the present invention.

However, to pull the thin suture element 200 with high force always brings the risks of e.g. cutting off gloves and hurt the fingers of the user. This is a very common problem that every surgeon faces in every surgery. The current solution is to make a roll with a couple of gauzes to hold the suture to pull. It is working, but it takes some time, sometimes it slips and needs a redo.

Therefore, the present invention also provided a tool 3 to standardize the suture pulling in order to ease the handling. Particularly, the tool 3 according to the present invention is adapted be used with the suspension device according to the present invention.

An embodiment of the tool 3 is shown in FIG. 11. According thereto, the suture pulling tool 3 has a handle 33 that may comprise a cylindrical shape, and a guide bar 30 that protrudes from the handle, particularly perpendicular to a longitudinal axis or cylinder axis of the handle 33. The tool 3 comprises two suture slots 31, 32 going through the guide bar 30 and handle 33, which slots are used to host the pulling sections 211, 212, 213.

Further, the tool comprises a first and a second actuation element 35, 36 (e.g. in the form of buttons) which are arranged on the handle 33.

These actuation elements 35, 36 are used to control clamps in the suture slots 31, 32 that are configured to hold or release the respective pulling section 211 or 212, 213 arranged in the respective slot 31, 32.

Further, the tool 3 comprises a distance probe 34 embedded in the guide bar 30, which can slide in and out of the guide bar 30 in the extension direction of the guide bar 30 and is used to measure the distance between a tip of the guide bar 30 and soft tissue M of the patient, particularly during pulling. Furthermore, there are two indicators 37, 38 embedded on a side of the guide bar 30 facing away from said slots 31, 32, namely a force indicator 37 and a distance indicator 38 for indicating a distance measure by the distance probe 34.

An exemplary use of the tool 3 according to FIG. 11 is shown in FIGS. 12 to 15.

Figure 12:
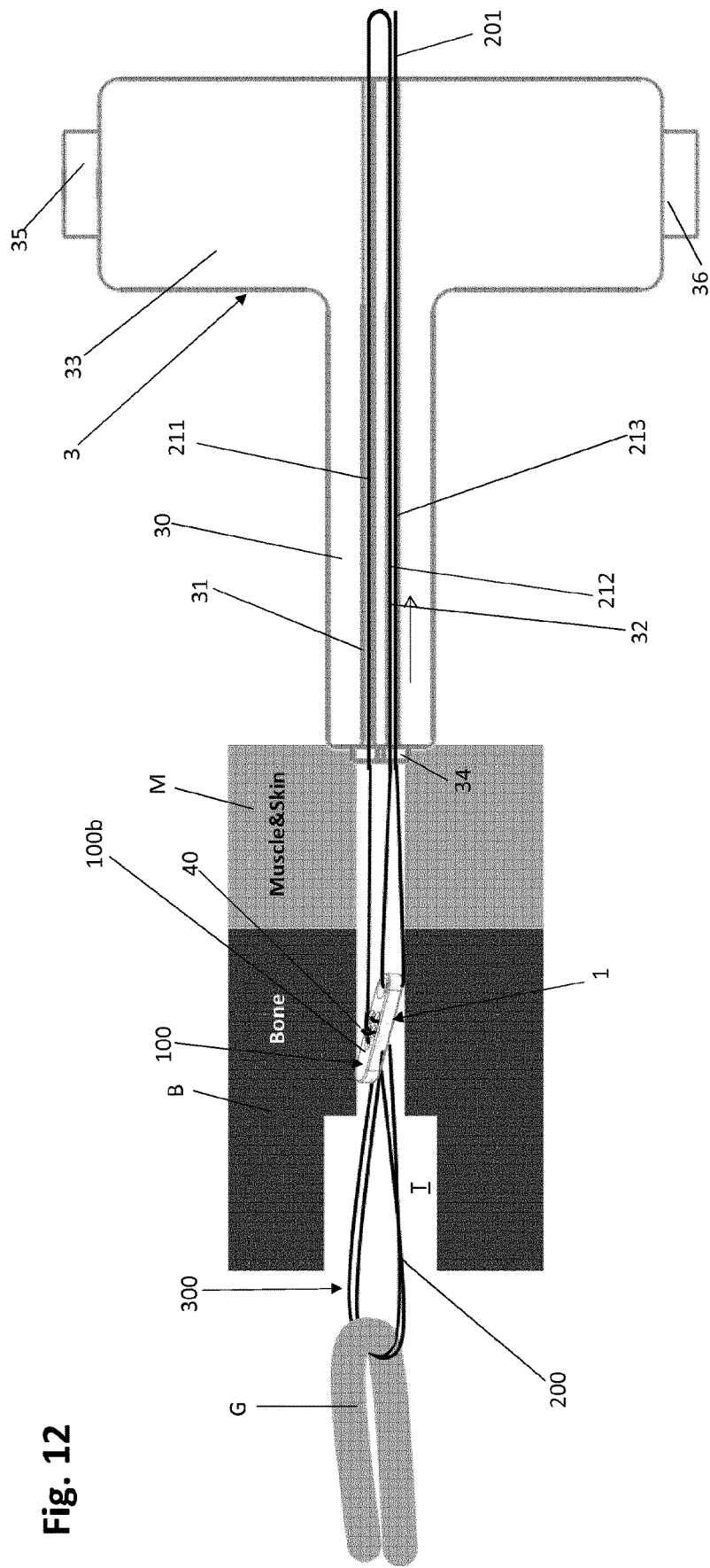

As shown in FIG. 12 the first pulling section 211 of the suture element 200 is arranged in the first slot of the tool while the second and the third pulling section 212, 213 are arranged in the second slot 32. The pulling sections 211, 212, 213 are clamped in the slots 31, 32 by operating the actuating elements 35, 36 in order to bring the suspension device 1 into the bone tunnel T. This step is correspondent with FIG. 6 without pulling tool 3.

Figure 13:
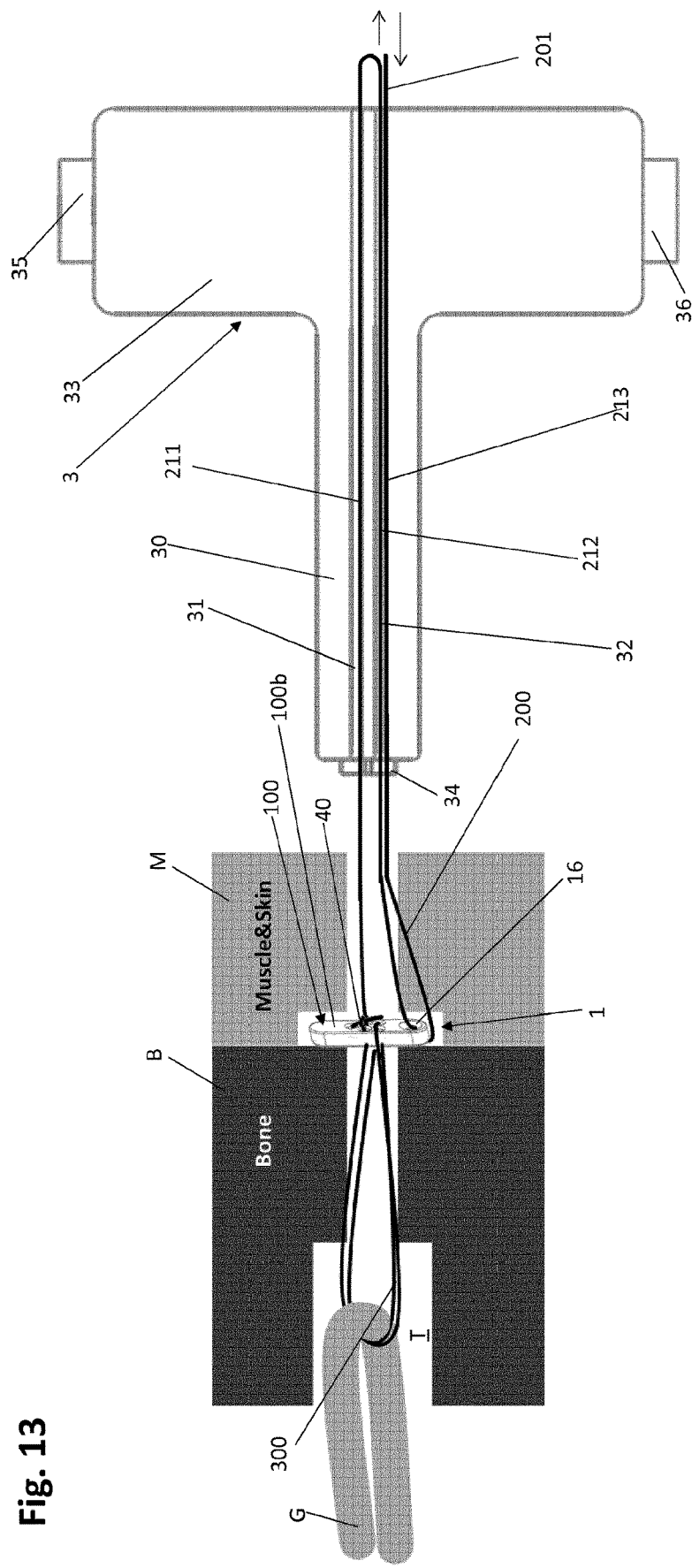

When the suspension plate 100 is outside of the bone tunnel T as shown in FIG. 13, the second slot is operated with the second actuating element 36 to release the second and the third pulling section 212, 213. Further, these pulling sections 212, 213 are removed from the suspension plate 100 and the second slot 32 of the tool 3. This step is correspondent with FIG. 7 without pulling tool.

Then, as shown in FIG. 14, the tool 3 is moved towards the skin M of the patient until the distance probe 34 touches the skin M. The first slot 31 is operated using the first actuating element 35 to hold the single first pulling section 211. This step is correspondent with FIG. 8 without pulling tool 3.

Further, as shown in FIG. 15, the distance probe 34 is then held in position at the skin M and the tool 3 is pulled away from the skin M to shorten the loops 301, 302, i.e. the suspension loop 300. When the graft G reaches a desired position, the pulling is stopped and the suture element 200/pulling section 211 is released from the first slot 31. The force exerted via the pulling section 211 and the distance generated upon pulling can be indicated using said indicators 37, 38. This step is correspondent with FIG. 9 without pulling tool.

To control holding and release of the pulling sections 211, 212, 213, the respective actuating element 35, 36 can be operated manually by the user. According to another embodiment, a distance can be pre-set into the tool 3 according to the bone tunnel length, wherein the distance probe 34 is now configured to trigger a respective actuating element automatically according to the pre-set distance. With this function, the surgeon does not need to worry about when the suspension plate is outside the bone tunnel, or when need to pull which pulling section. As long as the bone tunnel distance is measured and imported into the suture pulling tool 3, the actuating element (e.g. switch) to control holding and release of the pulling sections from the slots can be triggered automatically. The surgeon just pulls the tool 3 to the end, the rest is handled by the tool 3 automatically.

Further, FIG. 20 shows in conjunction with FIGS. 21 and 22 a further embodiment of a tool 3 according to the present invention.

Here, the distance probe 34b is slidably arranged in a guide bar 30b of the tool 3, wherein the tool 3 further comprises a handle 33c connected to the guide bar 30b. The distance probe 34b further comprises a distance probe handle 33b arranged at an end of the distance probe 34b to move the distance probe 34b relative to the guide bar 30b or handle 33c. With help of the handle 33b, the distance probe 34b is inserted into the bone tunnel T. A tip 203 of the guide bar 30b should be in direct contact with the cortical bone. The resulting distance between an end of the bone tunnel B and the tip of the distance probe 34b is known and will help the user to get information about the insertion depth of the distance probe 34.

The first end section 201 of the suture element 200 (i.e. the three pulling sections 211, 212, 213) is then guided through the first slot 31b and laced between a distance measuring wheel 38b (e.g. a rotational wheel with distance measuring function) and a force indicator 37b (e.g. a spring loaded nub with force measuring function dependent on suture tension) arranged on the guide bar 30b, the pulling sections 211, 212, 213 can be clamped by means of a self-locking clamp 35b mounted to the distance probe 34b.

As indicated in FIG. 21, as soon as the user feels a resistance during pulling on the pulling sections 211, 212, 213 of the suture element 200 by hand due to an interaction (e.g. contact) of the suspension plate 100 with the distance probe 34b, the user releases the second and third pulling sections 212, 213. Further, these pulling sections 212, 213 are removed from the suspension plate 100 to receive a single free (first) pulling section 211 coming from the suspension plate 100. After the first pulling section 211/first end section 201 is guided through the first slot 31b and laced between the distance measuring wheel 38b and the force indicator 37b it is clamped by means of the clamp 35b. Particularly, the clamp 35b can be formed as an (e.g. one-directional) self-locking cam cleat (cf. FIGS. 21 and 22).

If the distance probe handle 33b is now pulled in a lateral direction (i.e. away from the body/bone tunnel T) the suture element 200 will be tensioned resulting in compression of the force indicator 37b and indicating a certain force. If the force exceeds the total friction force (tool 3 friction and graft G friction within tunnel T) it will rotate the distance measuring wheel 38b and a displacement of the suture element 200 can be read off the wheel 38b. If the free first pulling section 211/first end section 201 is pulled, it will automatically flip the suspension plate 100 as soon as it reaches the outside of the bone B. The user can apply a certain pulling force on the handle 33b and read out if the force indicator 37b reaches a sufficient threshold. Finally, the user can cut the first pulling section 211/first end section 201 closely at the top of the bone B with a small rotating knife 204 which can be attached to the tool 3 and operated by a lever 205 hinged to the guide bar 30b or handle 33c.

Furthermore, besides ACL reconstruction, the present invention, particularly the embodiment shown in FIG. 16(A) (see also FIG. 4) can be used with a variety of different indications.

For instance, by adding a plate member 70 shown in FIG. 16 that may comprise two recesses 71, 72 (cf. FIG. 16(B)) or even four recesses 71, 72, 73, 74 (cf. FIG. 16(C) or 16(D)) two bones B, B' can be connected to one another as shown in FIG. 16 (E) or tension can be maintained on a single bone B as shown in FIG. 16(F).

By adding a second and a third plate member 80, 90, wherein each plate member 80, 90 may comprise two recesses 81, 82 or 91, 92, the device 1 shown in FIG. 17 (A) can be used to keep the tension between two bones B, B' as shown in FIG. 17(B). The further plate members 70, 80 or 90 can be pre-mounted with closed recesses (e.g. holes 71, 72; 73, 74, 81, 82, 91, 92), or can be mounted afterwards using open recesses as shown in FIGS. 16, 17. The potential indications are *varus* correction, lisfranc ligament repair, AC joint fixation, Syndesmosis repair, etc.

Furthermore, the shape of the suspension plate 100 can be adapted to the respective use/indication of the suspension device 1.

Particularly, according to a further embodiment of the suspension device 1 according to the present invention, which is shown in FIG. 18, the suspension device (cf. right hand side of FIG. 18) comprises an adapter plate 50, wherein the adapter plate 50 comprises a recess 51 for receiving the suspension plate 100 in a form fitting manner, particularly such that the through-holes 11, 12, 13, 14, 15, 16 are accessible from the front side 100a and from the rear side 100b of the suspension plate 100 when the letter is arranged in said recess 51 of the adapter plate 50. The adapter plate 50 can be designed to fit into a special bone tunnel T in a form fitting fashion.

Finally, FIG. 19 indicates an embodiment regarding fabrication of the stopper 20 that is arranged on the second end section 202 of the suture element 200.

According to FIG. 19, a stopper 20 can be formed, by conducting e.g. the following steps:
- cutting off a stiff end of the suture element 200 at the second end section 202 so as to expose individual fibers 23,
- particularly separating the fibers 23, e.g. to form them into a "mushroom" like shape
- heating the fibers 23 to merge the fibers 23 into a closed portion 22, particularly end 22, of the suture element 200,
- making a knot 21 (e.g. one strand self hitch) next to said portion/end 22
- putting the suture element 200 through a hole 61 of a plate 60
- pulling the first end section 201 of the suture element 200 to compress the knot 21
- removing the suture element 200 from the plate 60.

The invention claimed is:

1. An implantable suspension device (1) for fixing an elongated flexible implant (G) or tissue (B) in a desired position, comprising: a suspension plate (100) and a single suture element (200) engaging with the suspension plate (100) such that the suture element (200) forms an adjustable suspension loop (300) for connecting said implant (G) or tissue (B) to the suspension plate (100), wherein the single suture element (200) comprises a free first end section (201) and a second end section (202), and wherein the single suture element (200) comprises a stopper (20) arranged on the second end section (202), and wherein the suture element (200) forms a locking loop (40) for pressing the first end section (201) against the suspension plate (100) and thereby locking the first end section (201) of the suture element (200) with respect to the suspension plate (100), wherein the suspension plate (100) comprises a front side (100a) and a rear side (100b), which rear side (100b) faces away from the front side (100a), wherein the suspension plate (100) comprises a plurality of through-holes (11, 12, 13, 14, 15, 16), each through-hole (11, 12, 13, 14, 15, 16) extending from the front side (100a) to the rear side (100b) of said suspension plate (100), wherein said suture element (200) extends through each of said through-holes (11, 12, 13, 14, 15, 16), and wherein said plurality of through-holes (11, 12, 13, 14, 15, 16) is formed by six through-holes.

2. The implantable suspension device according to claim 1, characterized in that the suspension loop (300) is configured to be shortened by pulling on a first pulling section (211) formed by a portion of the first end section (201) of the suture element (200), which first pulling section (211) protrudes out of the locking loop (40).

3. The implantable suspension device according to claim 2, characterized in that a force loaded on the suspension loop (300) is proportionally related to a force applied on the first pulling section (211), and/or a change in length of the suspension loop (300) is proportionally related to a displacement of the first pulling section (211).

4. The implantable suspension device according to claim 2, characterized in that for reducing a loosening force ($F_{loosening}$) on the first pulling section (211) and supporting a self-locking of the suspension loop (300), the suspension loop comprises deflection points (P, P').

5. The implantable suspension device according to claim 2, characterized in that the suture element (200) is inserted such into said through-holes (11, 12, 13, 14, 15) that a pulling force (F) applied to the first pulling section (211) of the first end section (201) of the suture element (200) and transferred to the suspension loop (300) is at least amplified by a factor of four, and/or particularly such that said locking force ($F_L$) is a friction force with a pressing force at least twice as large as said pulling force (F) on the first pulling section (211) of the suture element (200).

6. The implantable suspension device according to claim 1, characterized in that the suture element (200) is inserted into a first through-hole (11) of said plurality of through-holes (11, 12, 13, 14, 15, 16) with the first end section (201) ahead such that the stopper (20) butts against the suspension plate (100) to prevent the suture element (200) from being completely pulled through the first through-hole (11) of the suspension plate (100).

7. The implantable suspension device according to claim 6, characterized in that the suture element (200) is furthermore successively inserted into a second through-hole (12), a third-through hole (13), a fourth through-hole (14) and a fifth through-hole (15) of said plurality of through-holes such that the adjustable suspension loop (300) is formed on the front side (100a) of the suspension plate (100) and/or such that the locking loop (40) is formed on the rear side (100b) of the suspension plate (100), wherein the first end section (201) of the suture element (200) is further inserted into the locking loop (40) for clamping the first end section (201) of the suture element (200) by means of the locking loop (40) to the rear side (100b) of the suspension plate (100) with a locking force ($F_L$).

8. The implantable suspension device according to claim 6, characterized in that said plurality of through-holes (11, 12, 13, 14, 15, 16) comprises a second through-hole (12), wherein the suture element (200) is inserted into the second through-hole (12) so that the locking loop (40) is formed on the rear side (100b) of the suspension plate (100).

9. The implantable suspension device according to claim 8, characterized in that said plurality of through-holes comprises a third through-hole (13), wherein the suture element (200) is inserted into the third through-hole (13) so that the first loop (301) of the suspension loop (300) is formed on the front side (100a) of the suspension plate (100).

10. The implantable suspension device according to claim 9, characterized in that said plurality of through-holes comprises a fourth through-hole (14), wherein the suture element (200) is inserted into the fourth through-hole (14).

11. The implantable suspension device according to claim 10, characterized in that said plurality of through-holes comprises a fifth through-hole (15), wherein the suture element (200) is inserted into the fifth through-hole (15) so that the second loop (302) of the suspension loop (300) is formed on the front side (100a) of the suspension plate (100).

12. The implantable medical suspension device according to claim 11, characterized in that said first end section (201) protruding out of the fifth through-hole (15) is inserted into said locking loop (40), wherein the portion of said first end section (201) of the suture element (200) protruding out of the locking loop (40) forms a first pulling section (211) of the suture element (200) for pulling on the suture element (200) so as to shorten the suspension loop (300).

13. The implantable medical suspension device according to claim 12, characterized in that said plurality of through-holes comprises a sixth through-hole (16), wherein said first end section (201) of the suture element (200) protruding out of the locking loop (40) is insertable into said sixth through-hole (16) to form second and third pulling sections (212, 213) extending from the sixth through-hole (16), respectively, for pulling the suspension device (1) through a bone tunnel (T).

14. The implantable suspension device according to claim 1, characterized in that the suspension loop (300) is a structure comprising a first loop (301) and a second loop (302) formed by the suture element (200).

15. The implantable medical suspension device according to claim 1, characterized in that the stopper (20) comprises at least one knot (21) formed in the second end section (202) of the suture element (200).

* * * * *